United States Patent
Porshinsky et al.

(10) Patent No.: US 9,314,260 B2
(45) Date of Patent: Apr. 19, 2016

(54) SURGICAL DEVICE, METHOD OF PERFORMING SURGERY USING SAME, AND SURGICAL DEVICE KIT

(76) Inventors: Brian S. Porshinsky, Chesterfield, MO (US); Richard D. Peters, Gahanna, OH (US)

( * ) Notice: Subject to any disclaimer, the term of this patent is extended or adjusted under 35 U.S.C. 154(b) by 548 days.

(21) Appl. No.: 13/696,279

(22) PCT Filed: May 4, 2011

(86) PCT No.: PCT/US2011/035170
§ 371 (c)(1),
(2), (4) Date: Feb. 20, 2013

(87) PCT Pub. No.: WO2011/140206
PCT Pub. Date: Nov. 10, 2011

(65) Prior Publication Data
US 2013/0165962 A1     Jun. 27, 2013

Related U.S. Application Data

(60) Provisional application No. 61/331,198, filed on May 4, 2010.

(51) Int. Cl.
*A61B 17/04* (2006.01)
*A61B 17/32* (2006.01)
(Continued)

(52) U.S. Cl.
CPC ... *A61B 17/320036* (2013.01); *A61B 17/32053* (2013.01); *A61B 17/32056* (2013.01); *A61B 2017/32006* (2013.01); *A61B 2017/320733* (2013.01)

(58) Field of Classification Search
CPC ............... A61B 17/320036; A61B 17/32053; A61B 17/32056; A61B 2017/32006; A61B 2017/320733; A61B 17/0466; A61B 17/0482
See application file for complete search history.

(56) References Cited

U.S. PATENT DOCUMENTS 2,833,284 A * 5/1958 Springer .................. 606/80
3,835,859 A    9/1974 Roberts
(Continued)

FOREIGN PATENT DOCUMENTS

WO   WO 2006/044727    4/2006

OTHER PUBLICATIONS

International Search Report.
(Continued)

*Primary Examiner* — Gregory Anderson
(74) *Attorney, Agent, or Firm* — Brian S. Porshinsky; Fay Sharpe LLP

(57) ABSTRACT

A surgical device for severing a targeted tissue structure embedded within biological tissue of a patient includes a solid needle having an elongated length and extending lengthwise between opposing first and second ends. The solid needle includes an outer surface and a needle cross-sectional dimension, A hollow needle is slidingly received along the solid needle. The hollow needle includes a needle passage having a passage cross-sectional dimension. A surgical filament is operatively connected to the solid needle and has a filament cross-sectional dimension. The passage cross-sectional dimension can be greater than the sum of the needle cross-sectional dimension and the filament cross-sectional dimension such that the solid needle and the surgical filament can co-extend through the needle passage in substantially freely sliding relation to the hollow needle. A surgical device kit and methods of use are also included.

7 Claims, 24 Drawing Sheets

(51) Int. Cl.
*A61B 17/3205* (2006.01)
*A61B 17/3207* (2006.01)

(56) References Cited

U.S. PATENT DOCUMENTS

| | | | |
|---|---|---|---|
| 4,678,459 | A | 7/1987 | Onik |
| 4,808,157 | A | 2/1989 | Coombs |
| 5,180,385 | A * | 1/1993 | Sontag ............... 606/224 |
| 5,522,826 | A | 6/1996 | Daily |
| 6,423,080 | B1 | 7/2002 | Gellman et al. |
| 7,189,240 | B1 * | 3/2007 | Dekel ............... 606/85 |
| 7,740,631 | B2 | 6/2010 | Bleich |
| 7,857,813 | B2 | 12/2010 | Schmitz et al. |
| 7,887,538 | B2 | 2/2011 | Bleich et al. |
| 8,048,080 | B2 | 11/2011 | Bleich et al. |
| 8,062,300 | B2 | 11/2011 | Schmitz et al. |
| 8,192,435 | B2 | 6/2012 | Bleich et al. |
| 2003/0171718 | A1 | 9/2003 | DeLegge et al. |
| 2004/0143280 | A1 * | 7/2004 | Suddaby ............... 606/167 |
| 2007/0055262 | A1 * | 3/2007 | Tomita et al. ............... 606/82 |
| 2008/0086034 | A1 | 4/2008 | Schmitz et al. |
| 2010/0004654 | A1 | 1/2010 | Schmitz et al. |
| 2010/0331883 | A1 | 12/2010 | Schmitz et al. |
| 2011/0046613 | A1 | 2/2011 | Schmitz et al. |
| 2011/0060314 | A1 | 3/2011 | Wallace et al. |
| 2011/0112539 | A1 | 5/2011 | Wallace et al. |
| 2011/0190772 | A1 | 8/2011 | Ashley et al. |
| 2011/0224710 | A1 | 9/2011 | Bleich |

OTHER PUBLICATIONS

Abstract of CHOW, "Endoscopic release of the carpal ligament: a new technique for carpal tunnel syndrome", Arthroscopy: The Journal of Arthroscopic and Related Surgery, 1989, pp. 19-24, vol. 5, Issue 1, Elsevier Inc., Mount Vernon, Illinois.

Abstract of CHOW, HANTES, "Endoscopic Carpal Tunnel Release: Thirteen Years' Experience With the Chow Technique", The Journal of Hand Surgery, Nov. 2002, pp. 1011-1018, vol. 27A No. 6, Mount Vernon, Illinois.

Mirza, King, "Newer techniques of carpal tunnel release", Orthopedic Clinics of North America, Apr. 1996, pp. 355-371, vol. 27 No. 2, New York.

* cited by examiner

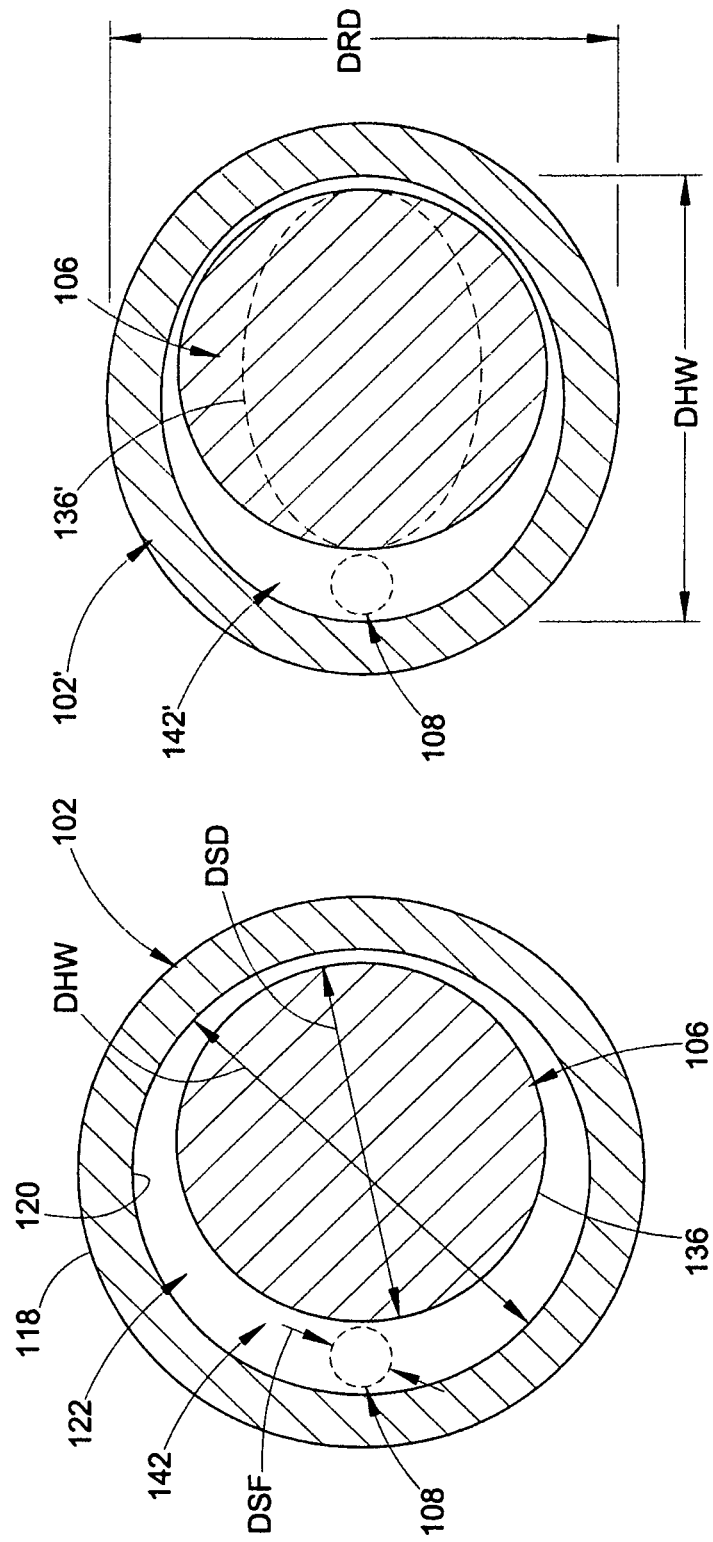

SURGICAL DEVICE, METHOD OF PERFORMING SURGERY USING SAME, AND SURGICAL DEVICE KIT

BACKGROUND

The subject matter of the present disclosure broadly relates to the art of surgical devices and procedures. More particularly, the subject matter of the present disclosure relates to surgical devices for severing tissue structures as well as methods of performing surgery that include the use of one or more of such surgical devices, and surgical device kits that contain one or more of such surgical devices.

The subject matter of the present disclosure may find particular use in connection with the performance of surgical procedures for treatment of compressive neuropathy and will be illustrated and described herein with specific reference thereto. As one example (and without limitation), the surgical devices, surgical procedures and surgical device kits of the subject application are illustrated and described herein in connection with the release of the transverse carpal ligament, which is more commonly referred to as carpal tunnel surgery, to treat compressive neuropathy occurring within the carpal tunnel. Other examples (and without limitation) of conditions in which the surgical devices, surgical procedures and surgical device kits of the subject application could be used include relief of ulnar tunnel syndrome, cubital tunnel syndrome, tarsal tunnel syndrome, tenosynovitis and tendonitis. However, it is to be understood that the subject matter of the present disclosure is capable of broad use in connection with a wide variety of other surgical procedures. As such, particular reference herein to use of the subject matter of the present disclosure in connection with carpal tunnel release is merely exemplary and not intended to be limiting.

As mentioned above, compressive neuropathies, tendonitis and tenosynovitis are physical conditions that are commonly treated through the performance of a surgical procedure. In some cases, an open technique may be used in which a portion of the tissue surrounding the targeted tissue structure is incised to expose the targeted tissue structure for direct view. Once exposed, the targeted tissue structure can be treated (e.g., transected) using appropriate surgical procedures. The surrounding tissue is then reapproximated using suitable surgical techniques. While certain advantages may exist with regard to the use of open techniques in the treatment of compressive neuropathies and other conditions, such procedures tend to result in substantial recovery time for patients and can involve elevated levels of patient discomfort during recovery.

As an alternative to open techniques, procedures have been developed that utilize endoscopic instruments during the treatment of the targeted tissue structure and that result in the incision of less of the surrounding tissue. In such cases, an incision is made adjacent the targeted tissue structure and an endoscopic instrument is inserted into the surrounding tissue in an area adjacent the targeted tissue structure. In this manner, the endoscopic instrument can be used to visualize the targeted tissue structure throughout the treatment procedure. A surgical tool, such as a hook knife, for example, that is operatively associated with the endoscopic instrument can then be used to treat the targeted tissue structure. However, certain disadvantages also exist with known endoscopic techniques. For example, endoscopic procedures typically provide less visual detail to the surgeon than open techniques. As such, additional care is often required to ensure that surrounding tissue structures, such as nerves and blood vessels, for example, are not altered during the endoscopic procedure. As another example, the level of visual detail that is available from known endoscopic techniques may also result in the less-than-complete treatment of the targeted tissue structure. In the case of procedures involving release of the transverse carpal tunnel, such a condition is sometimes referred to as "incomplete release."

As such, it is believed desirable to develop surgical devices, methods of performing surgery and surgical device kits in an effort to address one or more of the foregoing and/or other disadvantages of known surgical techniques.

BRIEF DESCRIPTION

One example of a surgical device in accordance with the subject matter of the present disclosure, such as may be used for severing a targeted tissue structure embedded within biological tissue of a patient, can include a solid needle having an elongated length and extending lengthwise between opposing first and second ends. The solid needle can include an outer surface and a needle cross-sectional dimension. A hollow needle can be slidingly received along the solid needle. The hollow needle can have an elongated length and can extend lengthwise between opposing first and second ends. The elongated length of the hollow needle can be less than the elongated length of the solid needle such that the hollow needle can be positioned along the solid needle with the first and second ends of the solid needle projecting outwardly beyond the first and second ends of the hollow needle. The hollow needle can include an inside surface at least partially defining a needle passage extending through the hollow needle from the first end to the second end. The needle passage can include a passage cross-sectional dimension. A surgical filament can have a length and can extend lengthwise between an attached end that is operatively connected to the first end of the solid needle and an opposing free end. The surgical filament can include a filament cross-sectional dimension. The passage cross-sectional dimension can be greater than the sum of the needle cross-sectional dimension and the filament cross-sectional dimension such that the solid needle and the surgical filament can co-extend through the needle passage in substantially freely sliding relation to the hollow needle.

Another example of a surgical device in accordance with the subject matter of the present disclosure, such as may be used for severing a targeted tissue structure embedded within biological tissue of a patient, can include a severing element that includes an elongated length of material capable of being positioned around the targeted tissue structure and within the biological tissue of the patient. The elongated length of material can extending lengthwise between opposing ends and can include a severing feature extending lengthwise along at least a portion thereof. The severing feature can be capable severing the targeted tissue structure upon the application of a force along at least one of the opposing ends.

A surgical device according to the foregoing paragraph can also include an elongated needle secured to one of the opposing ends of the elongated length of material of the severing element.

A surgical device according to the foregoing paragraph can further include an elongated needle secured to each of the opposing ends of the elongated length of material of the severing element.

A surgical device according to any one of the foregoing three paragraphs can include the elongated length of material being a first elongated length of material having a first leading end and a first trailing end, and the severing element including a second elongated length of material having a second leading end and a second trailing end. The second trailing end of the second elongated length of material being connected to the first leading end of the first elongated length of material.

A surgical device according to the foregoing paragraph can include the first elongated length of material including a length of metallic wire with the severing feature being formed by an abrasive outer surface along a portion of the length of metallic wire and the second elongated length of material including an echogenic wire.

A surgical device according to any one of the foregoing two paragraphs can include the severing element including a third elongated length of material having a third leading end and a third trailing end with the third trailing end being connected to the second leading end of the second elongated length of material. The third elongated length of material can be formed from a polymeric material.

One example of a surgical device in accordance with the subject matter of the present disclosure, such as may be used for tunneling into a targeted tissue structure embedded within biological tissue of a patient, can include an elongated hollow tube portion having a first end and an opposing second end. A handle portion can be disposed along the second end such that an elongated passage extends through the surgical device.

A surgical device according to the foregoing paragraph can include at least the first end of the elongated hollow tube portion being formed from an echogenic material.

One example of a surgical device in accordance with the subject matter of the present disclosure, such as may be used for protecting biological tissue of a patient during transfer of a severing element toward a targeted tissue structure embedded within the biological tissue of the patient, can include an elongated hollow tube having opposing open ends and a tube wall at least partially defining a passage in communication with the opposing open ends. The tube wall can include a window formed therethrough in communication with the passage. The window can be dimensioned to expose an associated severing feature of an associated severing element for engagement with the targeted tissue structure.

One example of a method in accordance with the subject matter of the present disclosure, such as for severing a targeted tissue structure embedded within biological tissue of a patient where the targeted tissue structure has a longitudinal extent, can include providing a severing element having an elongated length. The method can also include positioning the severing element at least partially around the targeted tissue structure such that the elongated length is disposed in transverse relation to the longitudinal extent of the targeted tissue structure. The method can further include drawing the severing element through the targeted tissue structure in a direction transverse to the longitudinal extent and thereby severing the targeted tissue structure.

A method according to the foregoing paragraph can also include the action of providing a severing element including providing a severing feature along the severing element, positioning the severing element includes positioning the severing feature adjacent the targeted tissue structure, and drawing the severing element through the targeted tissue structure includes reciprocating the severing element such that the severing feature is repeatedly moved through the targeted tissue structure.

Another example of a method according to the subject matter of the present disclosure, such as may be used for severing a targeted tissue structure embedded within biological tissue of a patient, can include identifying a targeted tissue structure to be severed. The method can also include extending a passage into the biological tissue adjacent the targeted tissue structure, and forming a lasso around the targeted tissue structure using a surgical filament with at least a portion of the surgical filament extending through the passage. The method can further include severing the targeted tissue structure using the surgical filament, and retracting the surgical filament from the biological tissue through the passage.

One example of a surgical device kit in accordance with the subject matter of the present disclosure can include a solid needle having an elongated length and extending lengthwise between opposing first and second ends. The solid needle can include an outer surface and a needle cross-sectional dimension. A hollow needle can have an elongated length and can extend lengthwise between opposing first and second ends. The elongated length of the hollow needle can be less than the elongated length of the solid needle such that the hollow needle can be positioned along the solid needle with the first and second ends of the solid needle projecting outwardly beyond the first and second ends of the hollow needle. The hollow needle can include an inside surface at least partially defining a needle passage extending through the hollow needle from the first end to the second end. The needle passage can include a passage cross-sectional dimension. A surgical filament can have a length and can extend lengthwise between a first end and an opposing second end. The surgical filament can include a filament cross-sectional dimension. The passage cross-sectional dimension can be greater than the sum of the needle cross-sectional dimension and the filament cross-sectional dimension such that the solid needle and the surgical filament can together extend through the needle passage in substantially freely sliding relation to the hollow needle.

Another example of a surgical device kit in accordance with the subject matter of the present disclosure can include a severing element that includes an elongated length of material capable of being positioned around a targeted tissue structure and within the biological tissue of a patient. The elongated length of material can extend lengthwise between opposing ends and can include a severing feature extending lengthwise along at least a portion thereof. The severing feature being capable severing the targeted tissue structure upon the application of a force along at least one of the opposing ends.

A surgical device kit according to the foregoing paragraph can also include soft-tissue tunneler that can include an elongated hollow tube portion having a first end and an opposing second end. Optionally, a handle portion can be disposed along the second end such that an elongated passage extends through the surgical device.

A surgical device kit according to either of the foregoing two paragraphs can include a guide filament formed from an elongated length of polymeric filament material.

A surgical device kit according to any of the foregoing three paragraphs can include an elongated needle having a pointed end and an elongated hollow needle having a blunt end. The elongated hollow needle dimensioned to receive therein both the elongated needle and at least a portion of the elongated length of material.

BRIEF DESCRIPTION OF THE DRAWINGS

FIG. 3A is a cross-sectional side view of the surgical device in FIG. 3 taken from along line 3A-3A thereof.

FIG. 3B is a cross-sectional side view of an alternate embodiment of the surgical device shown in FIGS. 3 and 3A.

DETAILED DESCRIPTION

Figure 1:
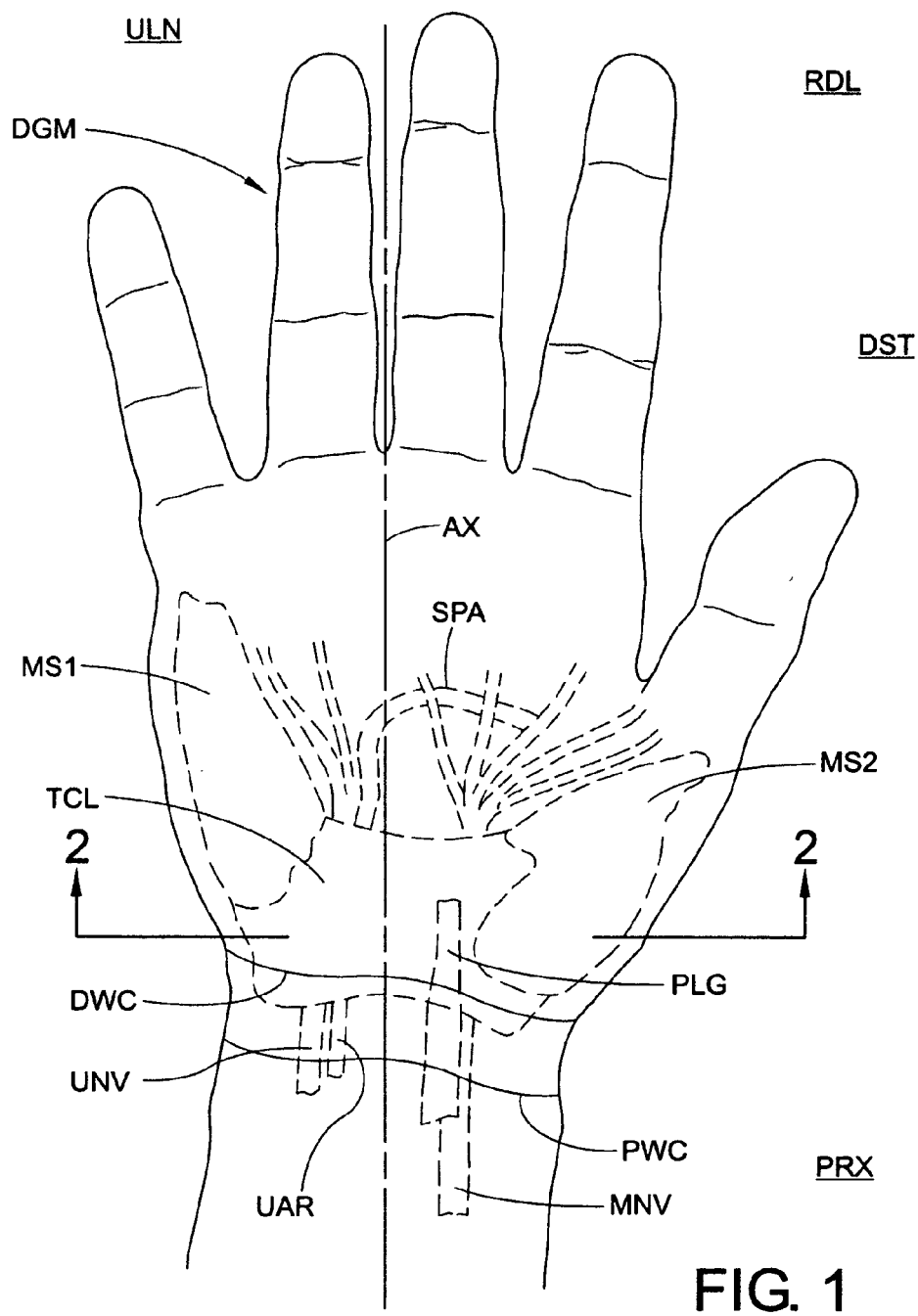
FIG. 1 is a palmar view of a human hand and wrist.
Figure 2:
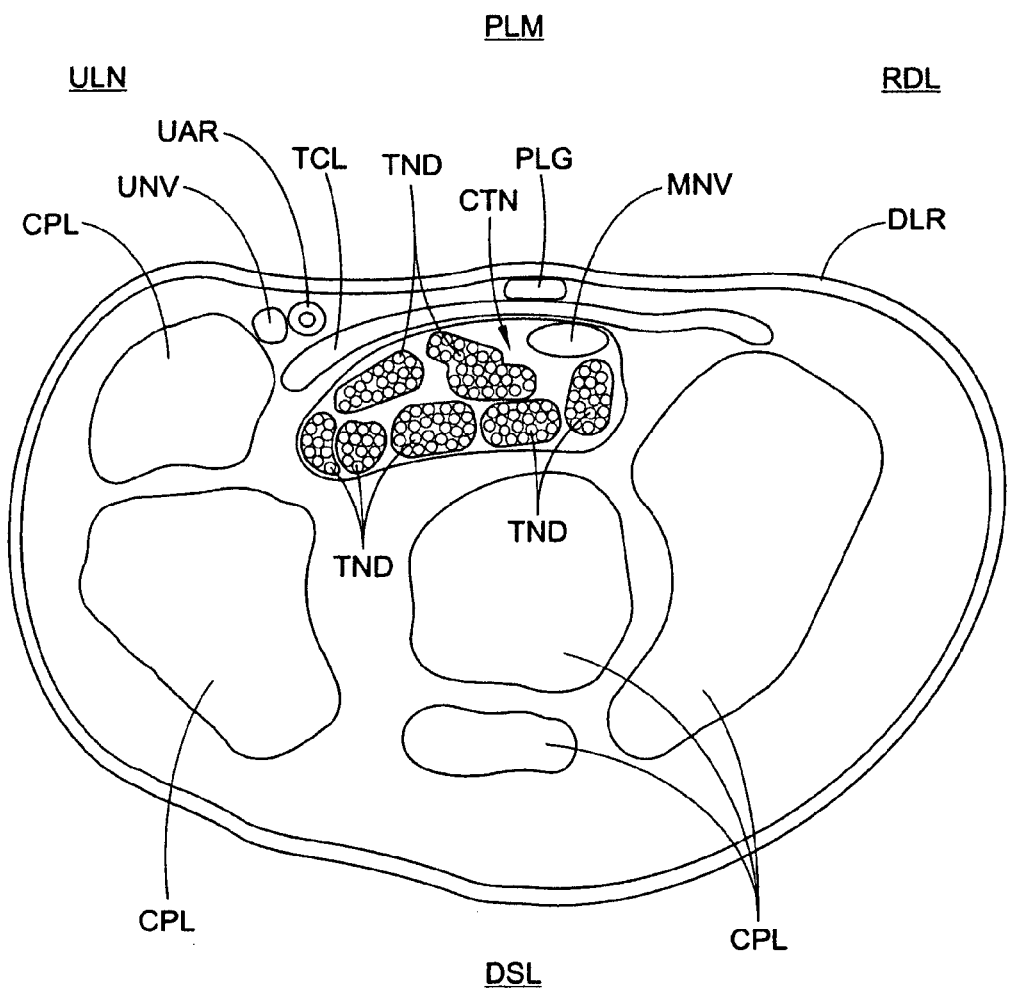
FIG. 2 is a transverse cross-sectional view of the human hand and wrist taken from along line 2-2 in FIG. 1.

With reference to FIGS. 1 and 2, a human hand and wrist are shown, in simplified form, with various tissue structures represented and identified. FIG. 1 is a palmar view of the human hand and wrist that includes representations of transverse carpal ligament TCL extending between muscle structure MS1, which is disposed ulnarly to ligament TCL, and muscle structure MS2, which is disposed radially to ligament TCL. Ulnar and radial directions are respectively represented in various drawing figures, including FIGS. 1 and 2, by reference characters ULN and RDL. Additionally, proximal and distal directions are respectively represented in various drawing figures, including FIGS. 1 and 2, by reference characters PRX and DST.

FIGS. 1 and 2 also include representations of distal wrist crease DWC and proximal wrist crease PWC. An axial line AX extends from the radial border of the digitus medicinalis DGM, which is also known as the ring finger, to a point along proximal wrist crease PWC ulnar to palmaris longus PLG. Ulnar artery UAR and ulnar nerve UNV are shown ulnar to axial line AX, and median nerve MNV is shown radial to axial line AX. Additionally, superficial palmar arch SPA is shown in FIG. 1 distal to transverse carpal ligament TCL.

FIG. 2 shows, in simplified form, various additional tissue structures that are not identified in FIG. 1, including the dermal layers (or skin), which are collectively represented in FIG. 2 by layer DLR. Additionally, palmar and dorsal directions are respectively represented in various drawing figures, including FIG. 2, by reference characters PLM and DSL. In some cases, the term anterior may be used instead of palmar and the term posterior may be used instead of dorsal. Carpal bones CPL are disposed outwardly and dorsally of transverse carpal ligament TCL such that carpal tunnel CTN is formed. Tendons TND and median nerve MNV extend through carpal tunnel CTN.

Figure 3:
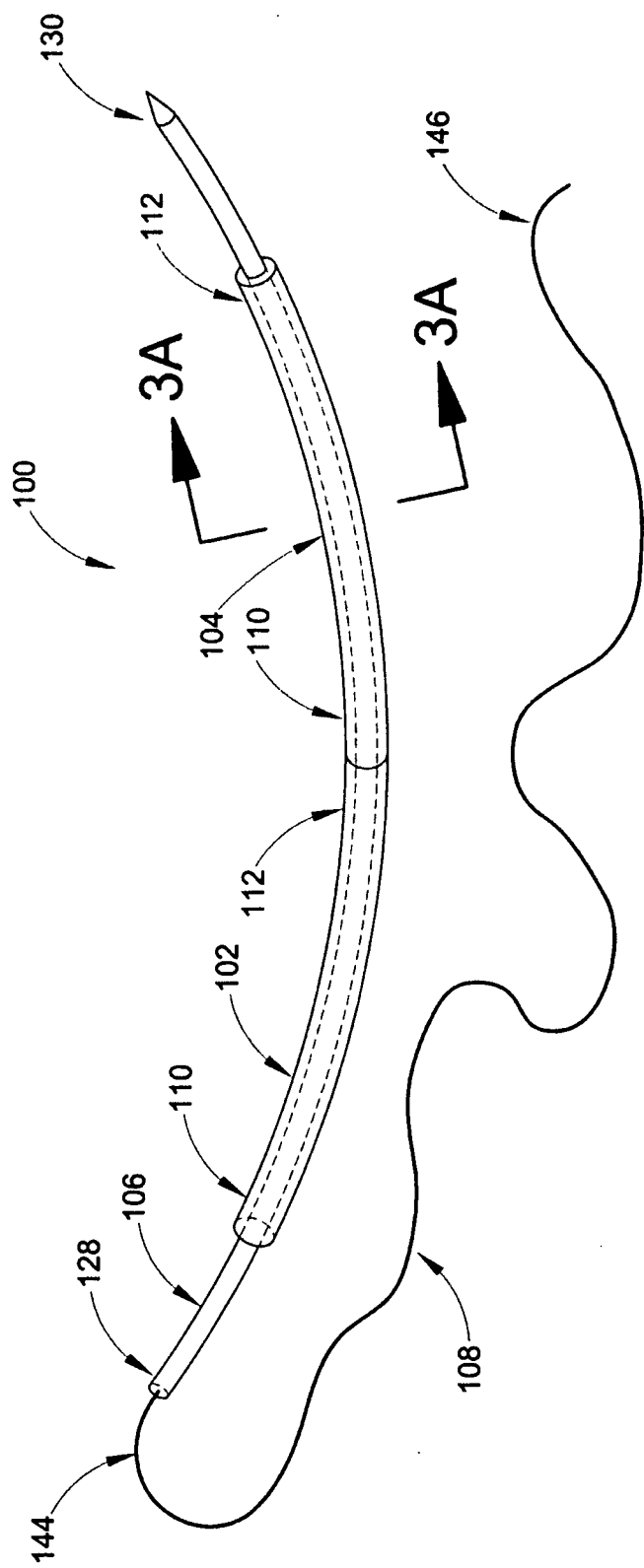
FIG. 3 is a side perspective view of one example of a surgical device in accordance with the subject matter of the present disclosure that includes at least one hollow needle, a solid needle and a surgical filament.
Figure 4:
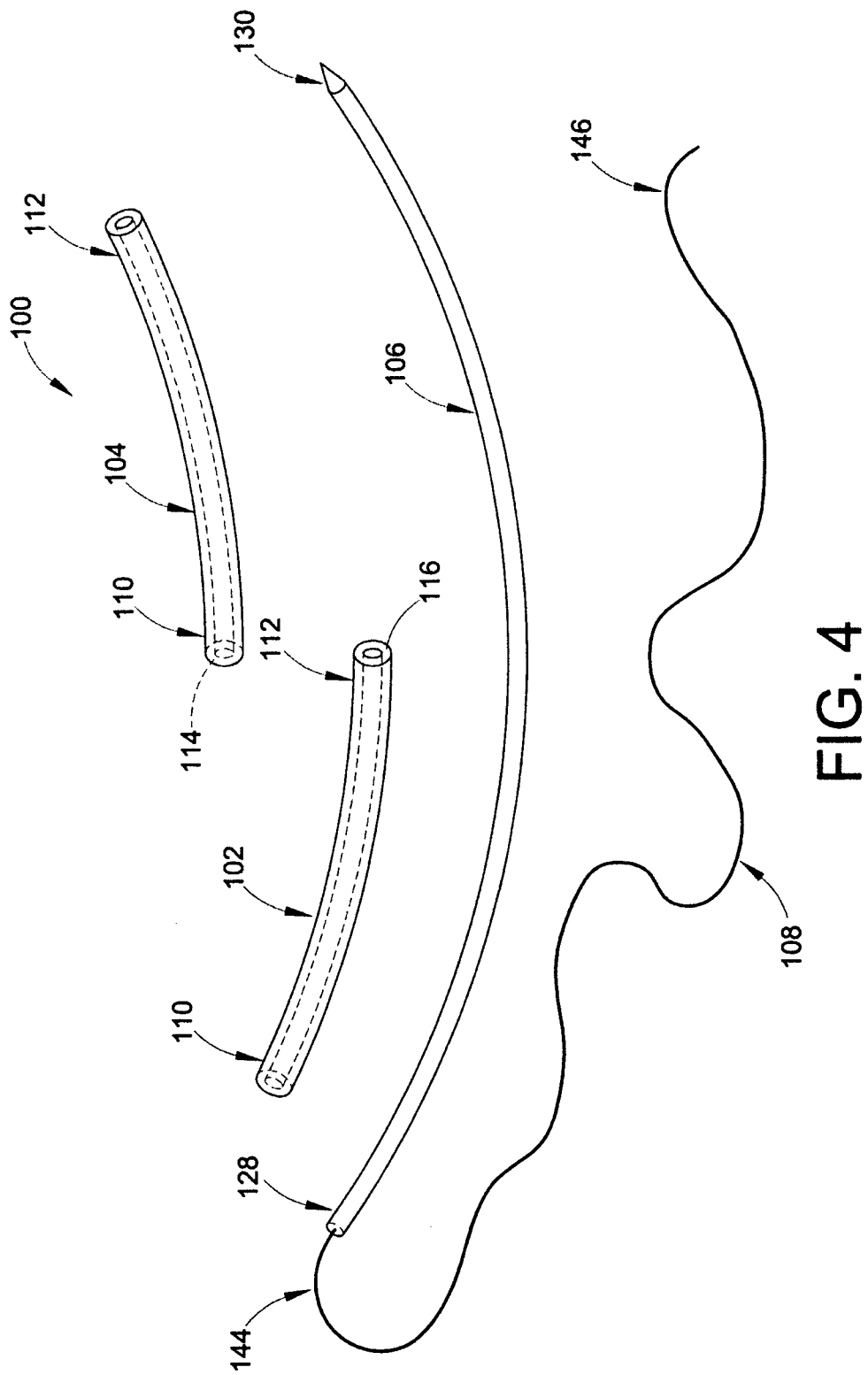
FIG. 4 is a side perspective view of one example of a surgical device kit in accordance with the subject matter of the present disclosure that includes at least one hollow needle, a solid needle and a surgical filament.

FIG. 3 illustrates one example of a surgical device in accordance with the subject matter of the present disclosure that includes at least one hollow needle, a solid needle and a severing element that is secured to the solid needle. It will be appreciated that, in some cases, the surgical device may include only one hollow needle. Whereas, in other cases, two or more hollow needles can be included in the surgical device. In the exemplary arrangement shown, surgical device 100 includes hollow needles 102 and 104, a solid needle 106 and a surgical filament 108. FIG. 4 illustrates surgical device 100 in a disassembled condition, such as may be provided as a surgical device kit, for example. Hollow needles 102 and 104 are shown in FIGS. 3 and 4 as being substantially identical to one another. It will be appreciated, however, that other arrangements could alternately be used in which two or more different hollow needles are included.

Figure 5:
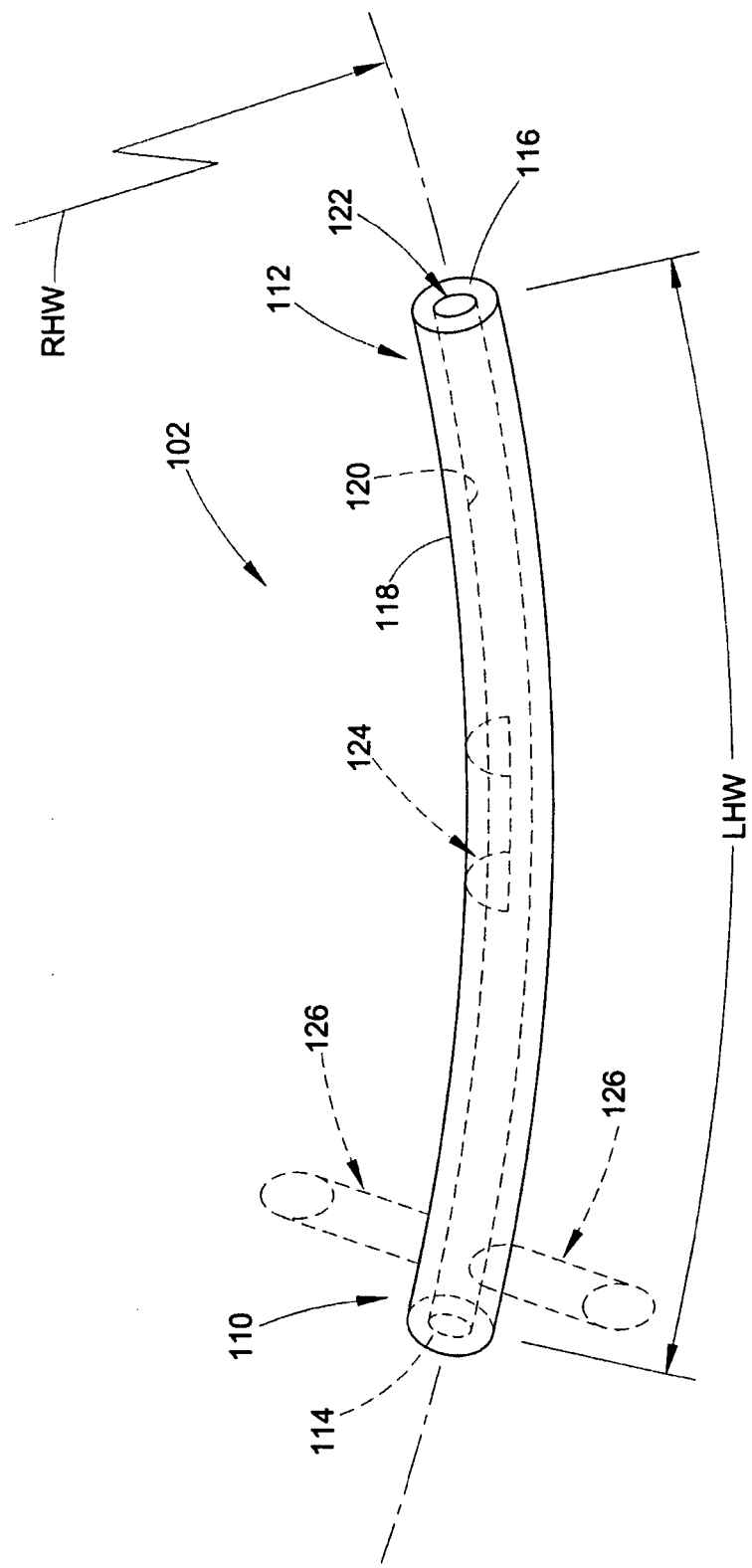
FIG. 5 is a side perspective view of one of the exemplary hollow needles in FIGS. 3 and 4.

Hollow needle 102, which can be substantially identical to hollow needle 104 in some cases, is shown in additional detail in FIG. 5. And, solid needle 106 and surgical filament 108 are shown in additional detail in FIG. 6. With reference, now, to FIGS. 3-6, hollow needles 102 and 104 each have a longitudinal length, which is represented in FIG. 5 by reference dimension LHW, and extend in a lengthwise direction between opposing ends 110 and 112. In some cases, one or both of ends can be tapered, curved or otherwise include a shape or profile. In the embodiments shown in FIGS. 3-5, the hollow needles terminate at opposing end walls 114 and 116 that are respectively disposed along ends 110 and 112. End walls 114 and 116 are shown as being approximately planar. As such, end wall 116 of hollow needle 102 is shown in FIG. 3 as being disposed in abutting engagement with end wall 114 of hollow needle 104.

As can be more clearly seen in FIG. 3A, hollow needle 102 (and hollow needle 104, which is not shown in FIG. 3A) can include an outer surface 118 and an inner surface 120 that at least partially defines a needle passage 122 that extends lengthwise along the hollow needle between the opposing open ends thereof. As shown in FIG. 5, hollow needles 102 and 104 can optionally include any one or more additional features and/or components that may improve the functionality and/or performance of the hollow needles. As one example, a window or opening 124 can optionally be provided on or along either or both of the hollow needles. Such an opening, if provided, would extend through the hollow needle into communication with needle passage 122 and, thus, may be useful for permitting a cutting element to engage a targeted tissue structure while shielding the cutting element from surrounding, non-targeted tissue. As another example, a handle 126 can optionally be provided on or along either of both of the hollow needles. It will be appreciated that such a handle, if provided, may be useful for guiding the hollow needles during surgical procedures and/or for retracting the hollow needles toward the end of the surgical procedure. Additionally, handles 126, if provided, can optionally be removably secured on or along the hollow needles in a suitable manner.

Figure 6:
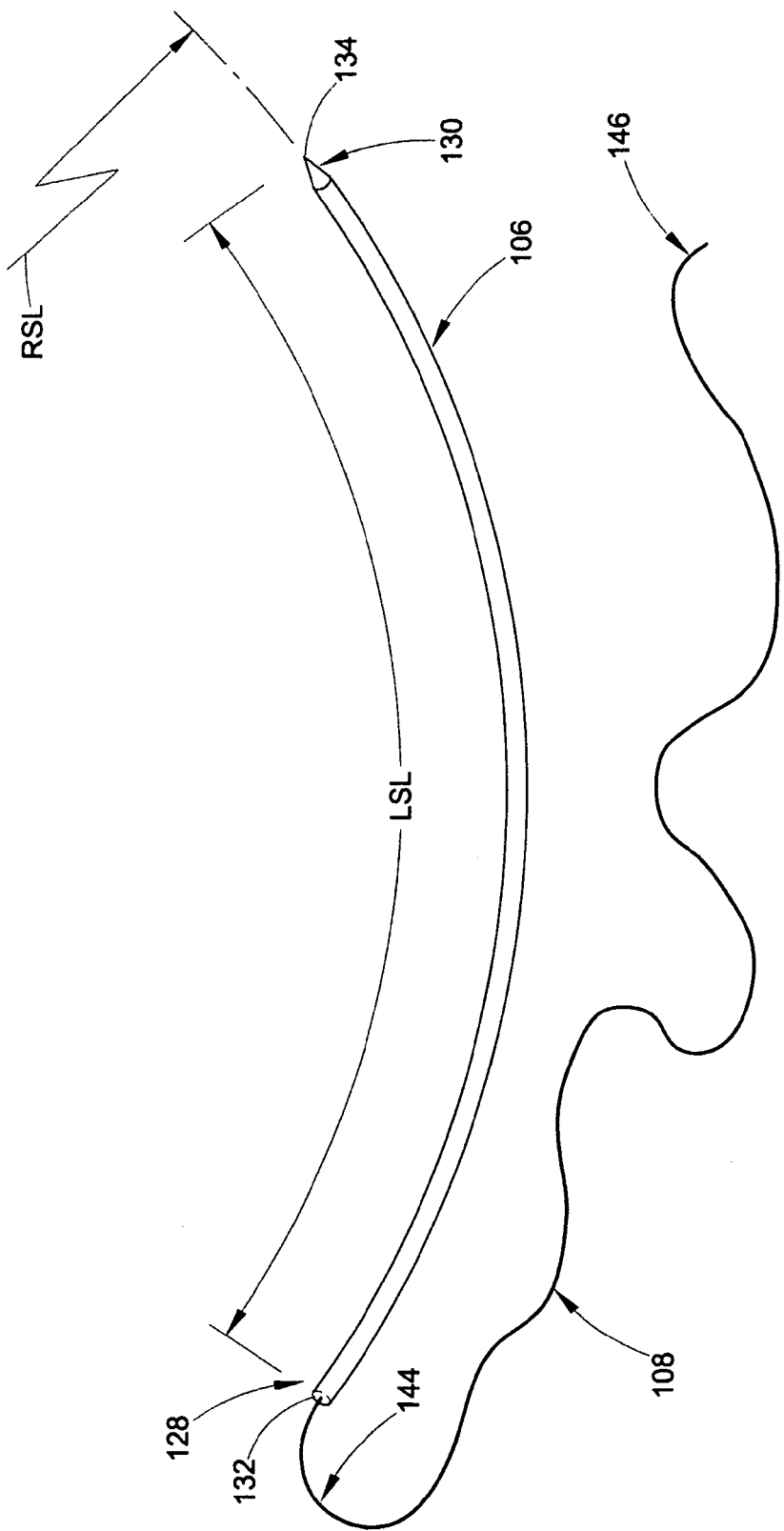
FIG. 6 is a side perspective view of the exemplary solid needle and surgical filament in FIGS. 3 and 4.

Solid needle 106 has a longitudinal length, which is represented in FIG. 6 by reference dimension LSL, and extends in a lengthwise direction between opposing ends 128 and 130. The ends of solid needle 106 can terminate in any suitable manner, such as, for example, by being sharply pointed, blunt or otherwise rounded, or approximately planar. In the embodiments shown in FIGS. 3-6, solid needle 106 includes an approximately planar wall 132 along end 128 and a sharp point 134 along end 130. As mentioned above, however, other configurations and/or arrangements could alternately be used. As identified in FIG. 3A, solid needle 106 also includes an outer surface 136 that extends along the length of the solid needle between ends 128 and 130.

It will be recognized from FIGS. 3-6 that hollow needles 102 and 104 are shown as being somewhat shorter in length in comparison with solid needle 106. In the assembled condition shown in FIG. 3, it is identifiable that the sum of the lengths of hollow needles 102 and 104 are less than the length of the solid needle. As a result, ends 128 and 130 respectively extend outwardly beyond end 110 of hollow needle 102 and end 112 of hollow needle 104.

Figure 7:
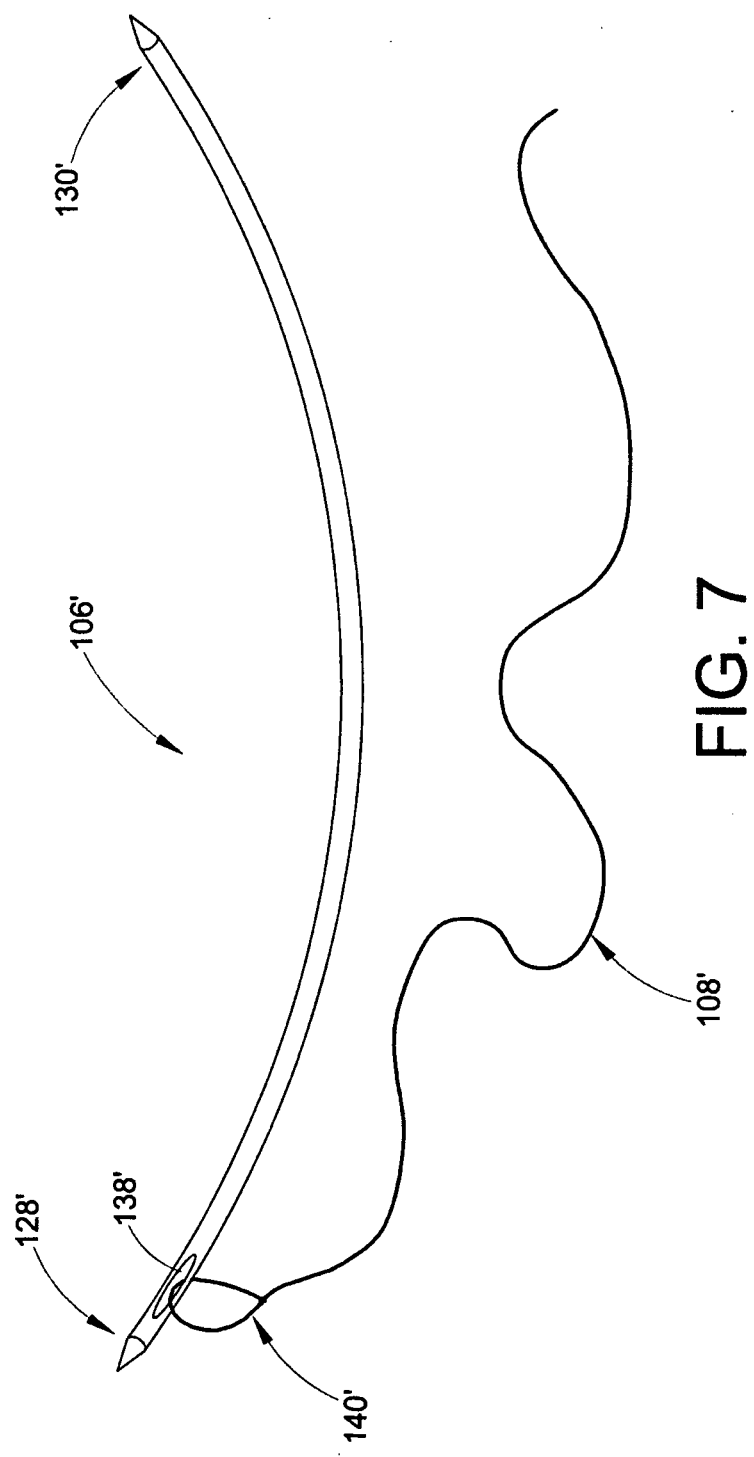
FIG. 7 is a side perspective view another example of a surgical device in accordance with the subject matter of the present disclosure that includes a solid needle with an eye and a surgical filament tied thereto.

In FIGS. 3, 4 and 6, surgical filament 108 is shown as being fixedly attached or otherwise secured to solid needle 106 along planar wall 132 thereof. It will be appreciated that any suitable connection or connector arrangement could be used to operatively secure the surgical filament to the solid needle. As mentioned above, the ends of the solid needle can terminate in any suitable manner. An alternate embodiment of a solid needle is shown in FIG. 7 as solid needle 106', which extends lengthwise between opposing ends 128' and 130'. Solid needle 106' differs from solid needle 106 in that solid needle 106' includes sharp point along end 128', rather than the planar wall of solid needle 106. Additionally, solid needle 106' includes an opening or eye 138' that extends through the solid needle in a direction generally transverse to the longitudinal length of the solid needle. Surgical filament 108' is shown as being secured to solid needle 106' using a suitable loop and knot arrangement 140'.

It will be appreciated that hollow needles 102 and 104 and solid needle 106 can be of any size, shape and/or configuration suitable for use in performing a procedure in accordance with the subject matter of the present disclosure. For example, the hollow and solid needles can be and, preferably, are of a substantially reduced cross-sectional size (e.g., diameter) in comparison with other instruments that are used to perform the aforementioned and other procedures. More specifically, the overall cross-sectional size of surgical device 100 can be less than approximately 5 mm, and, preferably, less than approximately 2.5 mm. In one specific example, an overall cross-sectional size of approximately 2 mm can be used.

While such small cross-sectional sizes are expected to result in significant improvements in patient recovery time and pain mitigation, in comparison with the use of conventional surgical devices (e.g., endoscopes) that are many times greater in size (e.g., 20-50 mm), it will be appreciated that the desired performance characteristics of a surgical device in accordance with the subject matter of the present disclosure, such as surgical device 100, for example, will vary from surgeon-to-surgeon. It is expected that some of the factors that may contribute or otherwise relate to the performance characteristics of the surgical device may include the elongated shape of the surgical device and flexibility of the surgical device as well as the flexibility of the individual components thereof. For example, in some cases, a surgeon may prefer a relatively straight surgical device that has a greater level of flexibility. In other cases, a surgeon may prefer a more curved shape on a surgical device that has a lesser level of flexibility (i.e., a higher level of rigidity). Accordingly, it will be appreciated that the shape of surgical device 100 and the components thereof shown in FIGS. 3-7 is merely illustrative and not intended to be in any way limiting. Additionally, it will be appreciated that any suitable material or combination of materials can be used to form surgical device 100 and the components thereof, such as metal (e.g., stainless steel) and/or medical grade plastics, and can be selected, treated or otherwise conditioned to provide the desired performance characteristics (e.g., flexibility).

Hollow needle 102 is shown in FIG. 5 as having a radius of curvature that is represented therein by radial dimension RHW. Similarly, solid needle 106 is shown in FIG. 6 as having a radius of curvature that is represented by radial dimension RSL. As shown in FIG. 3, hollow needles 102 and 104 can be slidingly received on or along the solid needle. As such, in one exemplary arrangement the radius of curvature of hollow needles 102 and 104 can be approximately equal to the radius of curvature of solid needle 106. In this manner, the hollow and solid needs can substantially freely slide relative to one another without interference from one another due to differences in curvature. In other cases, however, the curvature of the components could differ from one to another.

As mentioned above, it is desirable for the hollow and solid needles to be capable of sliding substantially freely relative to one another during use. As shown in FIG. 3A, hollow needle 102 has an approximately circular cross-sectional shape. As such, inner surface 120 defines a cross-sectional dimension of needle passage 122, which is represented by reference dimension DHW. Additionally, solid needle 106 also has an approximately circular cross-sectional shape. As such, outer surface 136 of hollow needle 106 defines a cross-sectional dimension of the solid needle, which is represented in by reference dimension DSD. It will be recognized and appreciated that the cross-sectional dimension of needle passage 122 is greater than the cross-sectional dimension of solid needle 106 such that a gap or space 142 is formed therebetween.

As discussed above, one benefit of a procedure in accordance with the subject matter of the present disclosure is the reduced invasiveness afforded by the subject technique and the subject surgical devices that are used in performing the subject technique. In an effort to further reduce the invasiveness of the process, a surgical device having a non-circular cross section could be used to potentially reduce the size of the surgical device in at least one direction. One example of such a configuration is illustrated in FIG. 3B and includes a hollow needle 102' having an approximately elliptical cross-sectional shape. Hollow needle 102' has an equivalent cross-sectional dimension DHW in at least one direction, as that of hollow needle 102 in FIG. 3A. However, hollow needle 102' can have a reduced outside cross-sectional dimension in the transverse direction, as is represented in FIG. 3B by reference dimension DRD. Additionally, or in the alternative, solid needle 106 could have a non-circular cross section, such as is represented in FIG. 3B by outer surface 136', for example. In any case, such a non-circular configuration will still result in a gap 142' formed between the solid and hollow needles.

During use in connection with a method or procedure in accordance with the subject matter of the present disclosure, a severing element in accordance with the subject matter of the present disclosure, such as a surgical filament, for example, is positioned around a targeted tissue structure within biological or body tissue. In some cases, such an action may be referred to herein as forming a lasso at least partially around the targeted tissue structure. The severing element can then be used to transect or otherwise sever the targeted tissue structure by pulling or drawing the surgical filament therethrough. In some cases, a reciprocal or sawing motion may be used. As such, at least a portion of a surgical filament in accordance with the subject matter of the present disclosure will be configured to function as a cutting element or device.

As one example of a severing element, surgical filament 108 (and 108') is shown in FIGS. 3, 4, 6 and 7 as having an elongated length that extends from one end 144 to an opposing end 146. In the exemplary arrangements shown, end 144 is operatively connected to an end of the solid needle and end 146 is free and unattached. Additionally, surgical filament 108 has a cross-sectional dimension that is generally represented in FIGS. 3A and 3B by reference dimension DSF. Furthermore, substantially the entire length of surgical filament 108 is shown as being configured to function as a cutting element or device. Further still, it will be recognized that surgical filaments 108 and 108' are shown and described herein as having a generally circular cross-sectional shape. However, it will be appreciated that a wide variety of other shapes and configurations could alternately be used. For example, the surgical filament could have a non-circular cross-sectional shape, such as a square, rectangular or elliptical shape. Additionally, the cross-sectional shape and/or size can, optionally, vary along the length of the surgical filament, such as by being tapered along at least a portion of the overall length.

Figure 8:
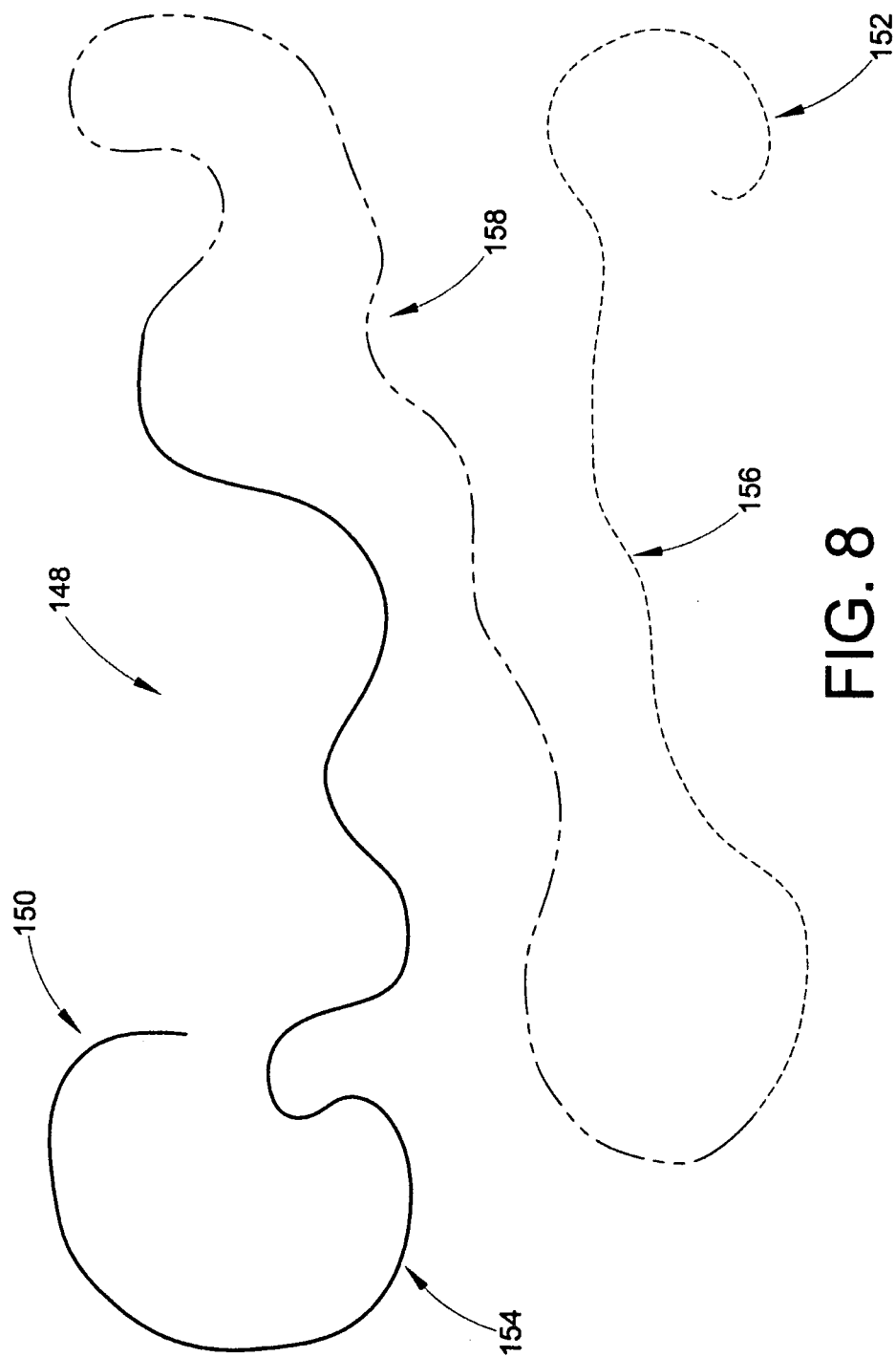
FIG. 8 is a top plan view of a further example of a surgical device in accordance with the subject matter of the present disclosure that includes a severing portion and a non-severing portion.

An alternate embodiment of a surgical filament 148 is shown in FIG. 8. Surgical filament 148 differs from surgical filament 108 in that surgical filament 148 includes a plurality of filament sections that can be configured to function in different manners for use throughout a method or procedure in accordance with the subject matter of the present disclosure. Surgical filament 148 has an elongated length that extends from one end 150 to an opposing end 152. Surgical filament 148 also includes a non-cutting filament portion 154 that is disposed along end 150 and extends toward end 152 and a cutting filament portion 156 that is disposed toward end 152 relative to non-cutting filament portion 154. Surgical filament 148 can also, optionally, include an echogenic filament portion 158 (or other filament construction that is amenable to use in association with an ultrasound or other visualization system).

It will be appreciated that the different filament portions can vary in cross-sectional size, shape and/or elongated length as well as other properties and characteristics, such as strength and/or flexibility, for example. As such, the construction of different filament portions can vary significantly from one another. For example, non-cutting filament portion 154 can be formed from a smooth, flexible length of material that has a relatively small cross-sectional size. In this manner, the non-cutting filament portion can be used to extend through the hollow needles together with the solid needle, such as is shown in FIGS. 3A and 3B, and form the lasso around the targeted tissue structure without exposing the surrounding tissue to a filament section that is configured for cutting. One example of a suitable material that could be used for non-cutting filament portion 154 is nylon mono-filament.

Additionally, as described above in connection with surgical filaments 108 and 108', it will be recognized that surgical filament 148 is shown and described herein as having a generally circular cross-sectional shape. However, it will be appreciated that a wide variety of other shapes and configurations could alternately be used. For example, the surgical filament could have one or more sections (or portions) that are of a non-circular, cross-sectional shape, such as a square, rectangular or elliptical shape. Additionally, it will be appreciated that any one or more of the plurality of portions can have a cross-sectional shape and/or size that can, optionally, vary along the length thereof, such as by being tapered along at least a portion of the overall length.

Once filament portion 154 has been formed into a lasso extending at least partially around the targeted tissue structure, cutting filament portion 156 can be drawn into position around the targeted tissue structure in preparation for transecting or otherwise severing the same. In some cases, a shield could, optionally, be used to prevent contact between the cutting filament portion and tissue surrounding the targeted tissue structure. Where a surgical filament having only a cutting portion, such as surgical element 108, for example, is used, the surgical filament is formed into a lasso around the targeted tissue structure directly. In some cases, a shield or other protective device may still be used. One example of a filament structure that would be suitable for use as cutting filament portion 156 and/or surgical element 108 is metal wire that has been coated with diamond particles. It will be appreciated, however, that other cutting filaments could alternately be used.

In some cases, a surgical filament having a visualization filament portion, such as echogenic filament portion 158 of surgical filament 148, for example, may be used. In such cases, the visualization filament portion can be positioned between the non-cutting filament portion and the cutting filament portion. In this manner, as the non-cutting filament portion is being drawn out of the body tissue from around the targeted tissue structure, the visualization filament portion will be drawn into and around the targeted tissue structure prior to the entry of the cutting filament portion. A visualization check can be performed using the visualization filament portion to ensure that the surgical filament is located in the desired position before the severing action is performed. One example of a filament construction that could be used as a visualization filament portion is sometimes referred to echogenic wire.

Figure 9:
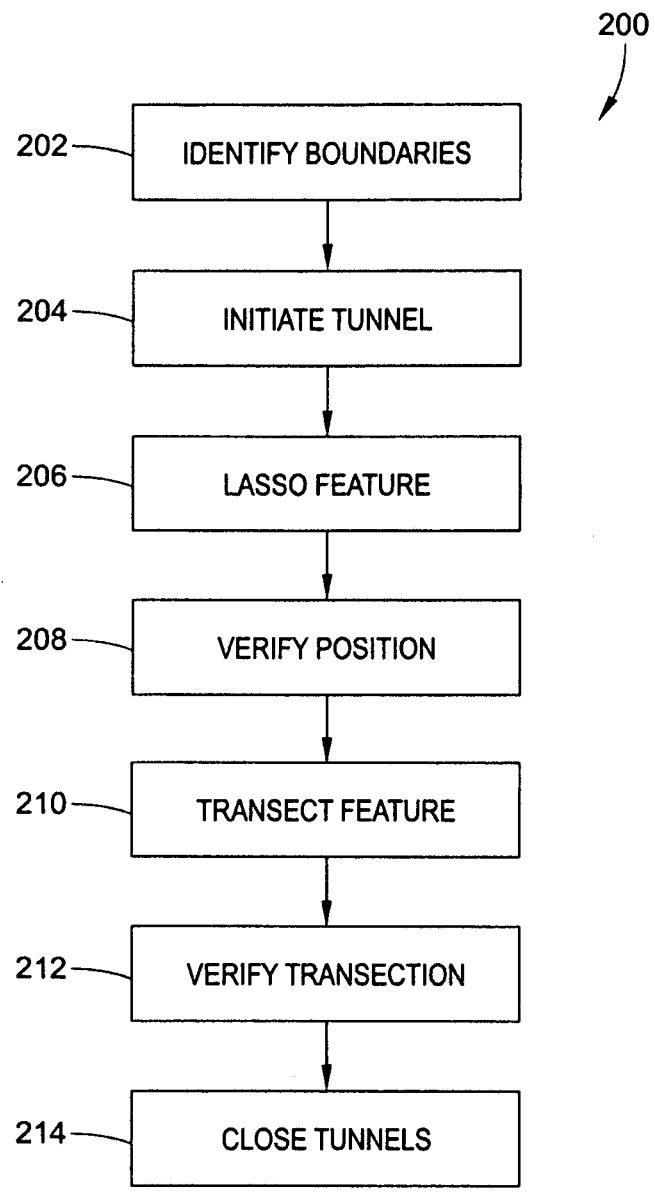
FIG. 9 is a graphical representation of one example of a method of performing a surgical procedure in accordance with the subject matter of the present disclosure.
Figure 10:
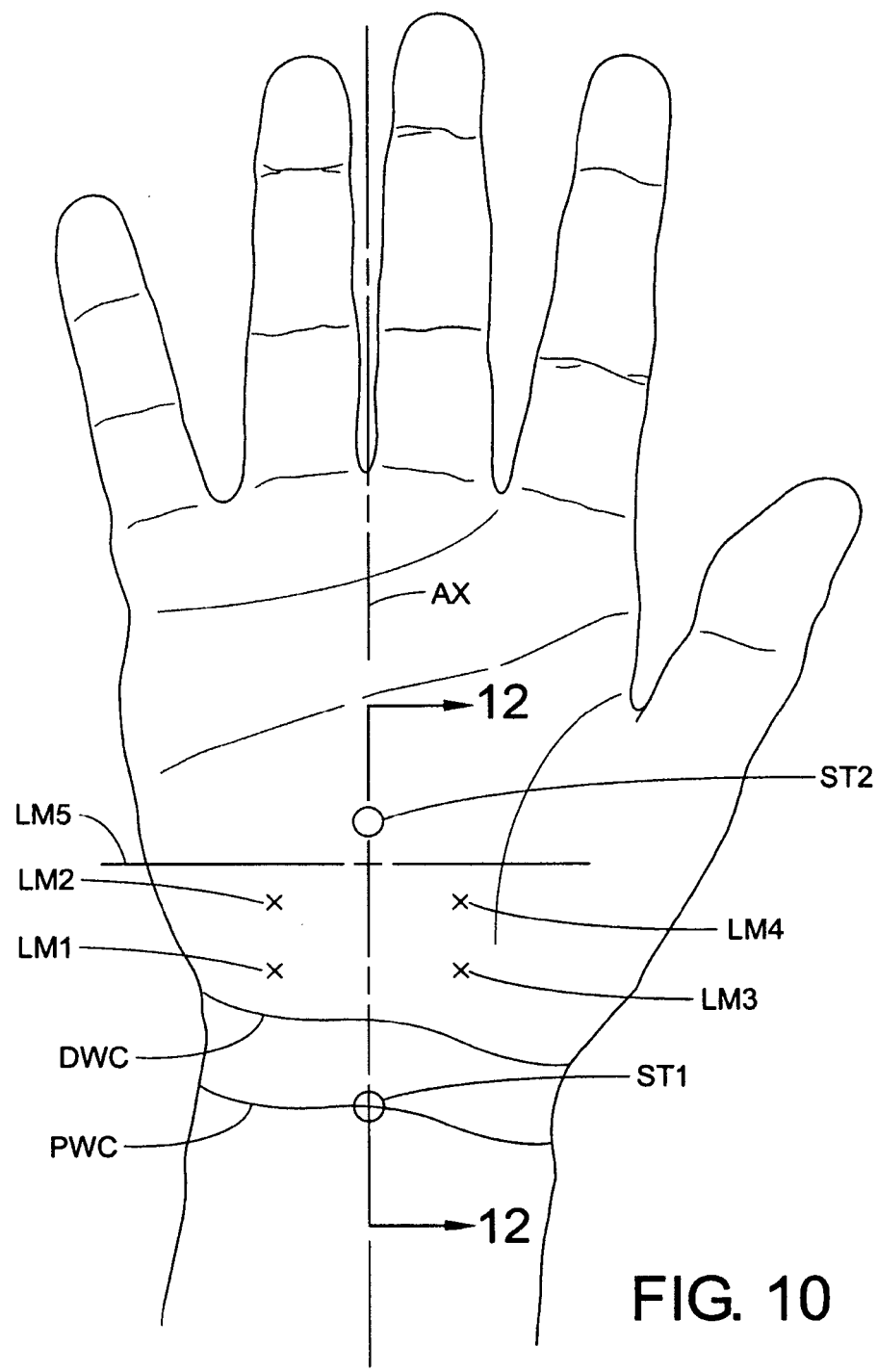
FIG. 10 is a palmar view of a human hand and wrist illustrating the identification of tissue structures and boundaries.

FIG. 9 is a graphical representation of one example of a method 200 of performing a surgical procedure in accordance with the subject matter of the present disclosure. Method 200 can include an initial step of identifying boundaries and landmarks surrounding and/or otherwise associated with the targeted tissue structure, such as represented by reference number 202 in FIG. 9. Such an initial step can be performed in any suitable manner, such as by visual and tactile inspection of the body structure and/or though the use of visualization modalities, such as ultrasound, for example. In the case of a procedure to release the transverse carpal ligament, certain boundaries and landmarks that can be used are identified in FIG. 10, as proximal wrist crease PWC, distal wrist crease DWC, pisiform LM1, hook of hamate LM2, tubercle of scaphoid LM3, tubercle of trapezium LM4, axial line AX, distal aspect of transverse carpal ligament LM5, tunnel site ST1 at intersection of the axial line and the proximal wrist crease, and tunnel site ST2 at intersection of axial line AX and a line 1 cm distal to distal aspect LM5.

Figure 11:
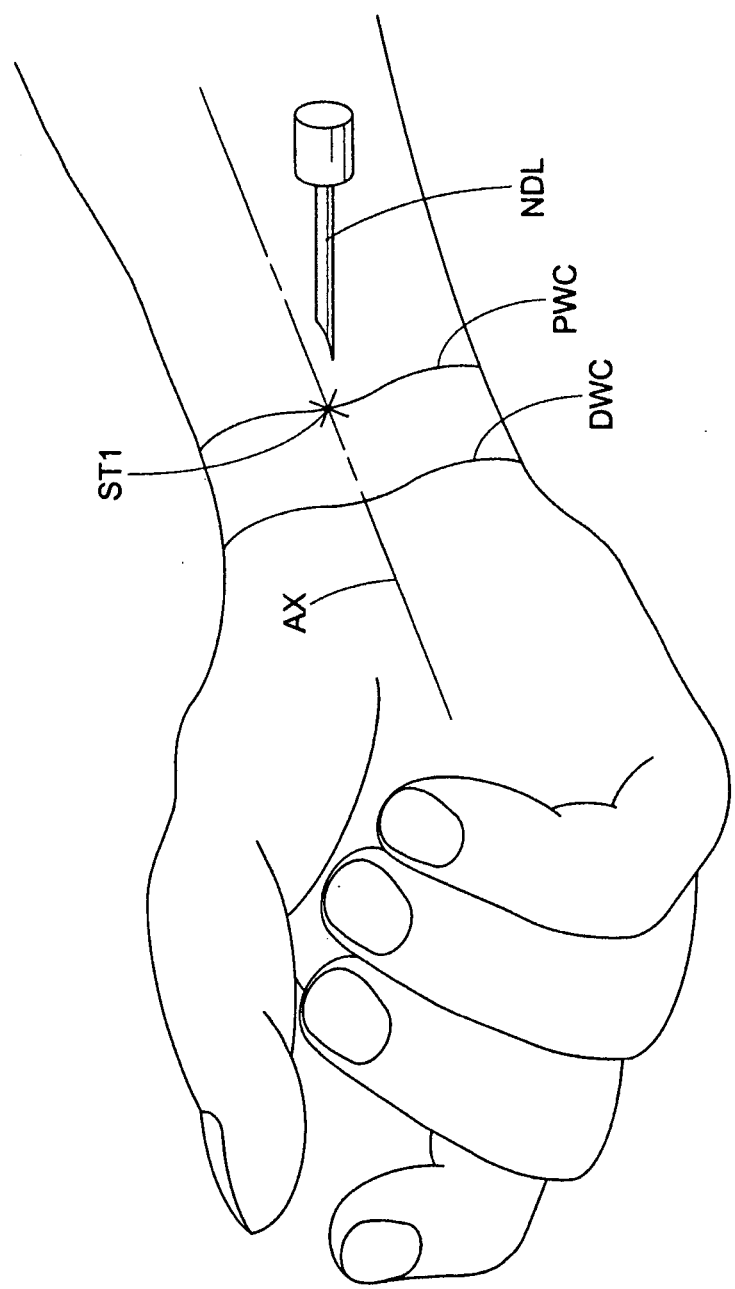
FIG. 11 is a palmar view of a human hand and wrist illustrating the creation of a stab incision at the insertion site identified in FIG. 10.
Figure 12:
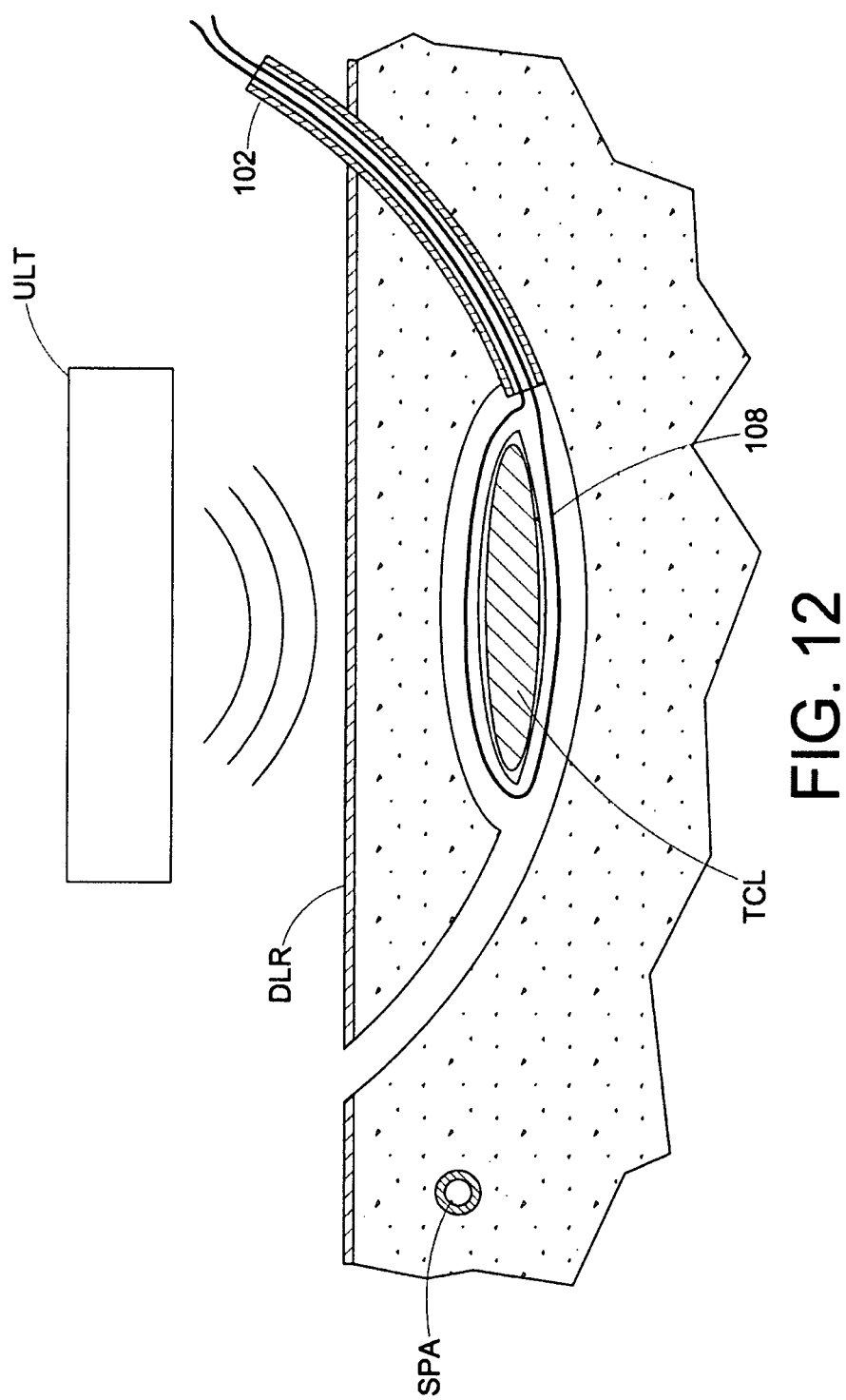
FIG. 12 is a cross-sectional side view, in simplified form, of the transverse carpal ligament and surrounding tissues taken from along line 12-12 in FIG. 10 showing a surgical filament forming a lasso around the targeted tissue structure.

Method 200 can also include an optional step of initiating a tunnel, such as is represented in FIG. 9 by reference number 204. If performed, such a tunnel can be initiated at a suitable site, such as tunnel site ST1, for example, as is shown in FIG. 11. Additionally, it will be appreciated that the tunnel can be initiated in any suitable manner, such as through the use of a conventional needle NDL or other tunneling device, for example. Method 200 also includes a step of at least partially lassoing the targeted tissue structure using a surgical filament, such as is represented by reference number 206 in FIG. 9. One example of a targeted tissue structure, such as a transverse carpal ligament TCL, is shown in FIG. 12 as being lassoed using a surgical filament, such as surgical filament 108, for example. In such an example, a passage can be formed into the body tissue adjacent the targeted tissue structure, such as is represented by hollow needle 102 in FIG. 12. Surgical filament 108 can extend through and out of the passage in the hollow needle, at least partially around the targeted tissue structure and can then return out of the body tissue through the hollow needle. It will be appreciated, however, that the foregoing is merely one example of a procedure for lassoing a targeted tissue structure, and that other sequences and/or steps could alternately be used.

Figure 13:
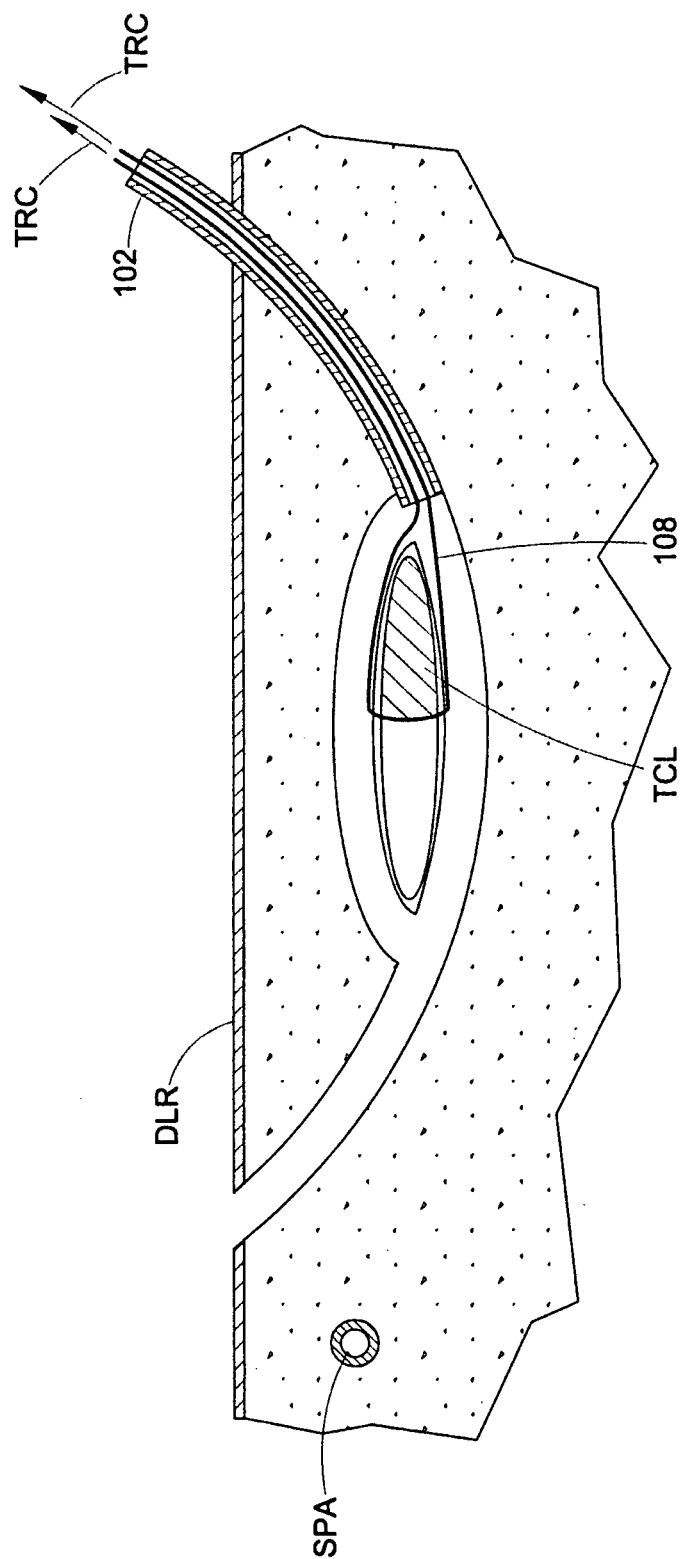
FIG. 13 is a cross-sectional side view, in simplified form, of the transverse carpal ligament and surrounding tissues in FIG. 12 showing the targeted tissue structure partially transected by the surgical filament.

Method 200 can also, optionally, include a step of verifying the position of the surgical filament to help ensure that the targeted tissue structure is captured within the lasso and that minimal non-targeted tissue captured, such as is represented in FIG. 9 by reference number 208. As shown in FIG. 12, an ultrasonic visualization system ULT can be used to perform this step. It will be appreciated, however, that other visualization modalities could alternately be used. Method 200 also includes a step of transecting or otherwise severing the targeted tissue structure, such as is represented by reference number 210 in FIG. 9. One example of an action of transecting a targeted tissue structure, such as a transverse carpal ligament TCL, is represented in FIG. 13 by arrows TRC shown pulling surgical filament 108 through the targeted tissue structure, such as through hollow needle 102, for example.

Figure 14:
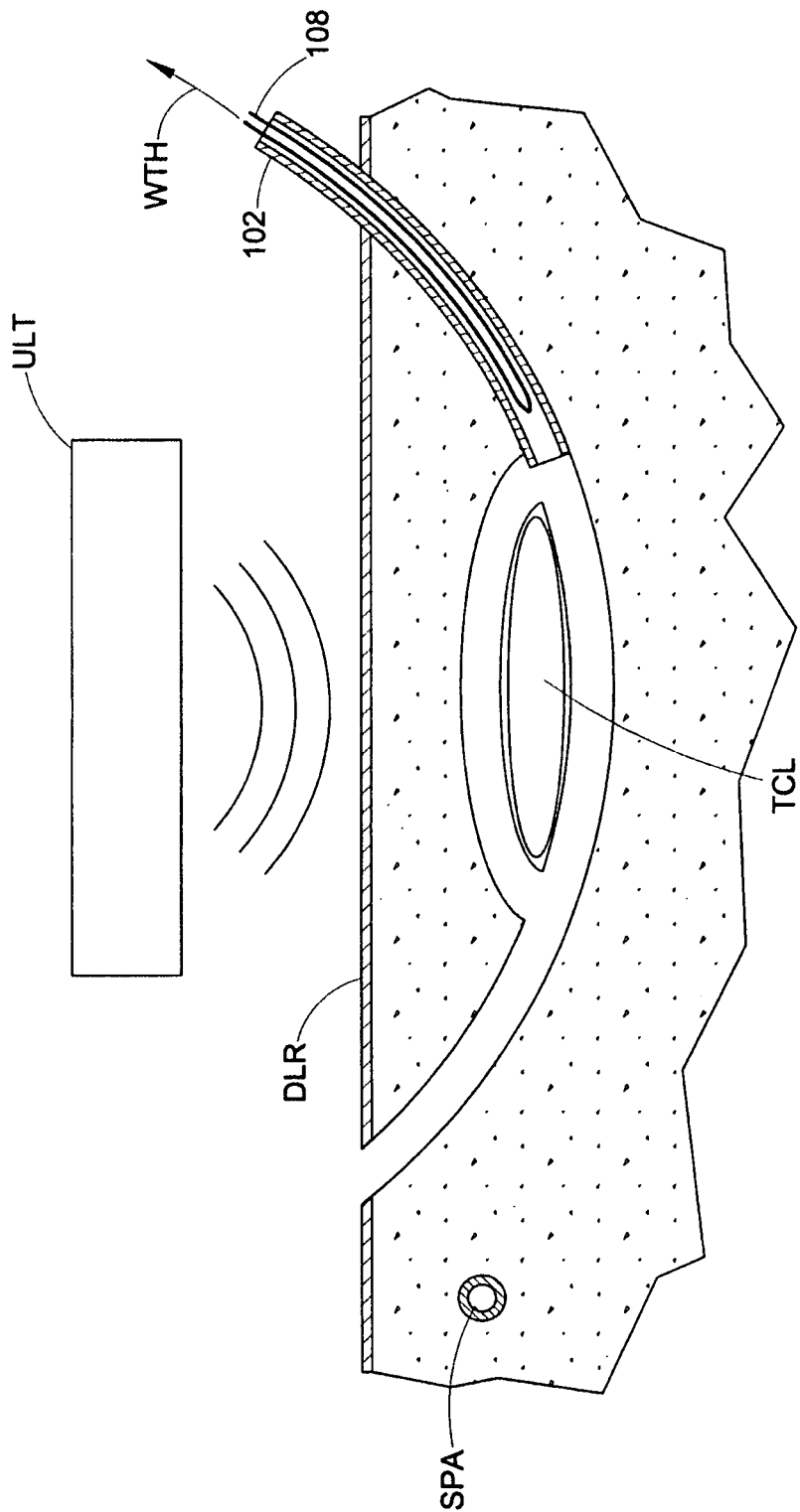
FIG. 14 is a cross-sectional side view, in simplified form, of the transverse carpal ligament and surrounding tissues in FIGS. 12 and 13 showing the targeted tissue structure fully transected by the surgical filament.

Method 200 can also, optionally, include a step of verifying that the targeted tissue structure has been fully severed, such as is represented in FIG. 9 by reference number 212. As shown in FIG. 14, an ultrasonic visualization system ULT can be used to perform this step. It will be appreciated, however, that other visualization modalities could alternately be used. Method 200 can further include a step of retracting the surgical filament and any additional surgical instruments and closing the one or more tunnels, such as is represented by reference number 214 in FIG. 9. For example, surgical filament 108 and hollow needle 102 can be withdrawn from the body tissue, as is represented by arrows WTH, in FIG. 14. The tunnels can then be closed using suitable surgical techniques.

Figure 15:
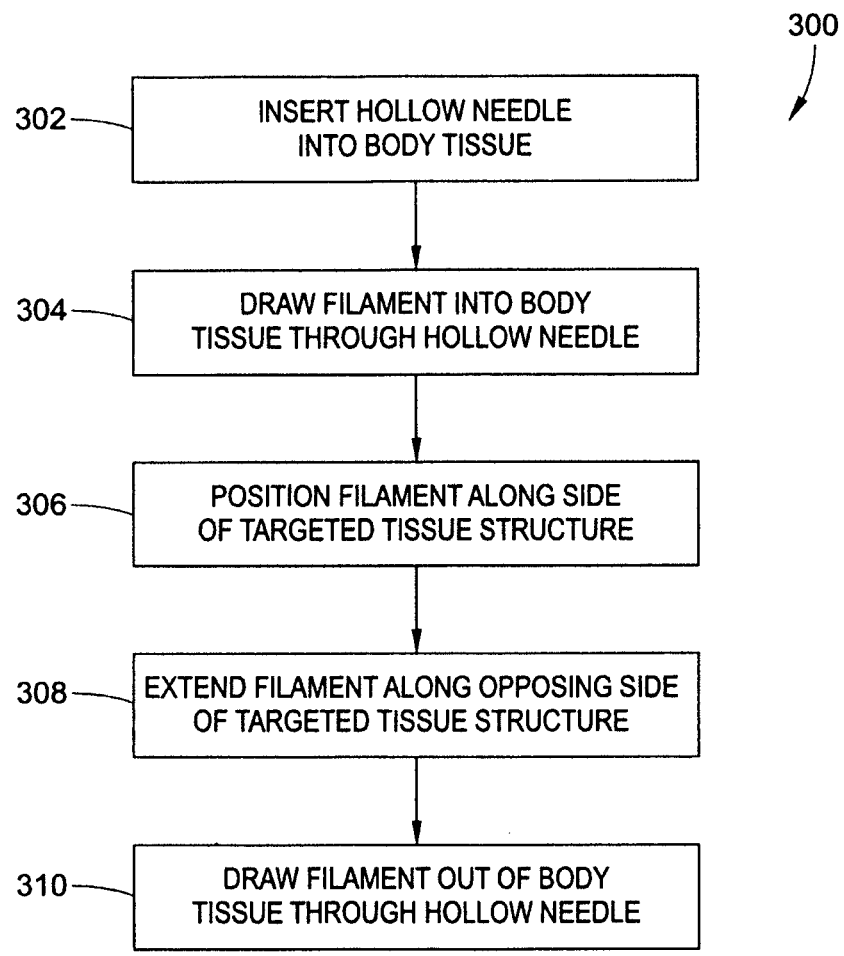
FIG. 15 is a graphical representation of one example of a method of lassoing a targeted tissue structure in accordance with the subject matter of the present disclosure.

It will be appreciated that the action or step of lassoing the targeted tissue structure using a severing element, such as one of surgical filaments 108, 108' and/or 148, for example, and such as is represented by reference number 206 in FIG. 9, can be performed in any suitable manner and through the performance of one or more additional actions or steps. One example of a method 300 of lassoing a targeted tissue structure using a surgical filament is shown in FIG. 15 as including an action or step of inserting a hollow needle into biological or body tissue, as is represented by reference number 302 in FIG. 15. Method 300 can also include pulling or otherwise drawing a portion of a surgical filament into the body tissue through the hollow needle, such as is represented in FIG. 15 by reference number 304, for example. Method 300 can further include positioning a portion of the surgical filament along one side of the targeted tissue structure, such as is represented by reference number 306 in FIG. 15. Method 300 can also include extending the surgical filament around the targeted tissue structure to the opposing side thereof, such as is represented in FIG. 15 by reference number 308. Method 300 can further include drawing a portion of the surgical filament out of the biological or body tissue through the hollow needle, as is indicated by reference number 310 in FIG. 15.

Figure 16:
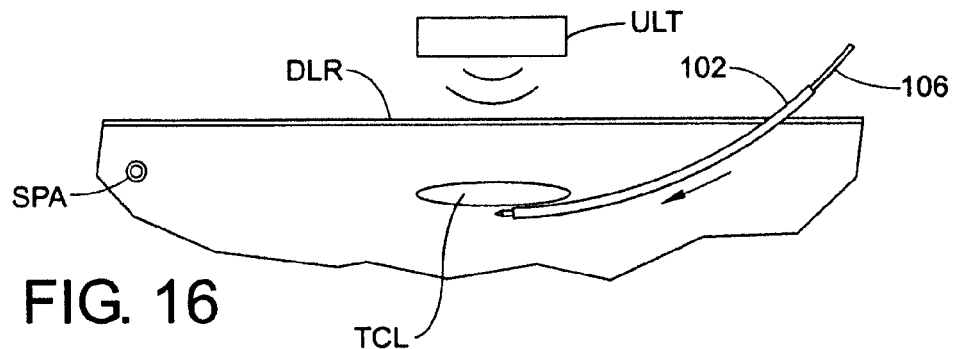
FIGS. 16-24 are cross-sectional side views, in simplified form, of the transverse carpal ligament and surrounding tissues in FIGS. 12-14 illustrating one example of a method of forming a lasso at least partially around a targeted tissue structure in accordance with the subject matter of the present disclosure.

The foregoing description of method 300 together with the graphical representation thereof illustrated in FIG. 15 broadly characterize certain actions and/or steps that can be taken to at least partially lasso a targeted tissue structure using a surgical filament. FIGS. 16-24 illustrate one example of a series of actions that can be performed to at least partially lasso a targeted tissue structure in such a manner. More specifically, FIG. 16 illustrates a portion of a first or proximal surgical device that includes a solid needle, such as solid needle 106, for example, and a hollow needle, such as hollow needle 102, for example, that are inserted together through dermal layers DLR from a point proximal to transverse carpal ligament TCL (e.g., site ST1 in FIG. 10) and into the biological or body tissue along a dorsal side of ligament TCL. A visualization system, such as ultrasonic system ULT, can be used to guide the placement of the solid and hollow needles relative to the ligament and other tissue structures. As one example, such an action can broadly correspond to reference number 302 of method 300.

Figure 17:
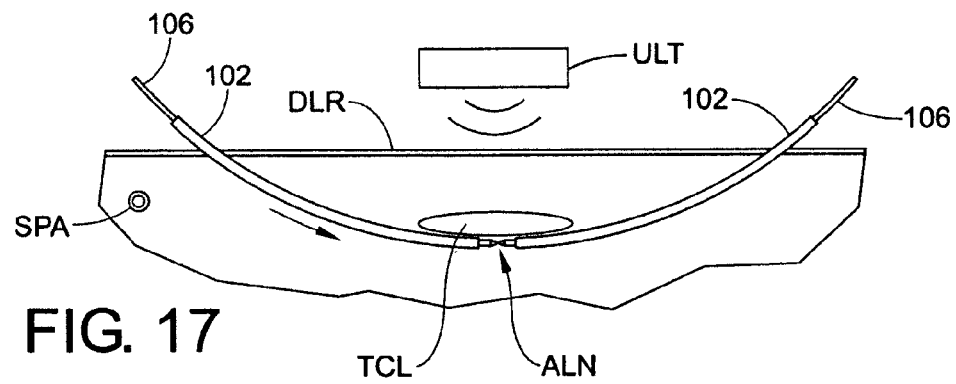

FIG. 17 illustrates a portion of a second or distal surgical device that includes a solid needle, such as solid needle 106, for example, and a hollow needle, such as hollow needle 102, for example, and are inserted together through dermal layers DLR from a point distal to transverse carpal ligament TCL (e.g., site ST2 in FIG. 10) and into the biological or body tissue along a dorsal side of ligament TCL. A visualization system, such as ultrasonic system ULT, can be used to guide the placement of the solid and hollow needles relative to the ligament and other tissue structures. Additionally, the visualization system can be used to at least approximately align the needle passages of hollow needles 102 with respect to one another, such as is identified in FIG. 17 by arrow ALN.

Figure 18:
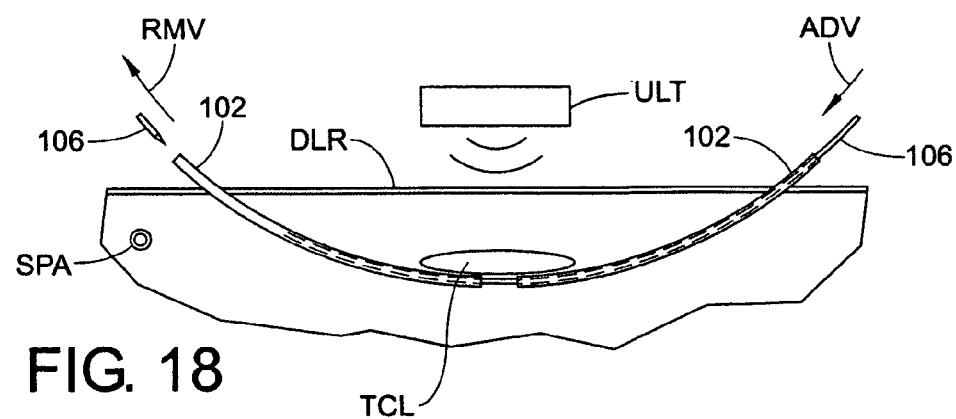

FIG. 18 illustrates solid needle 106 of the second surgical device being removed from hollow needle 102, as Is indicated by arrow RMV, with the hollow needle remaining in position within the body tissue. Additionally, solid needle 106 of the first surgical device is shown as being advanced distally into and along the needle passage of hollow needle 102 of the second surgical device, as is indicated by arrow ADV in FIG. 18. A visualization system, such as ultrasonic system ULT, can be used to guide the entry of solid needle 106 into hollow needle 102 of the second surgical device.

Figure 19:
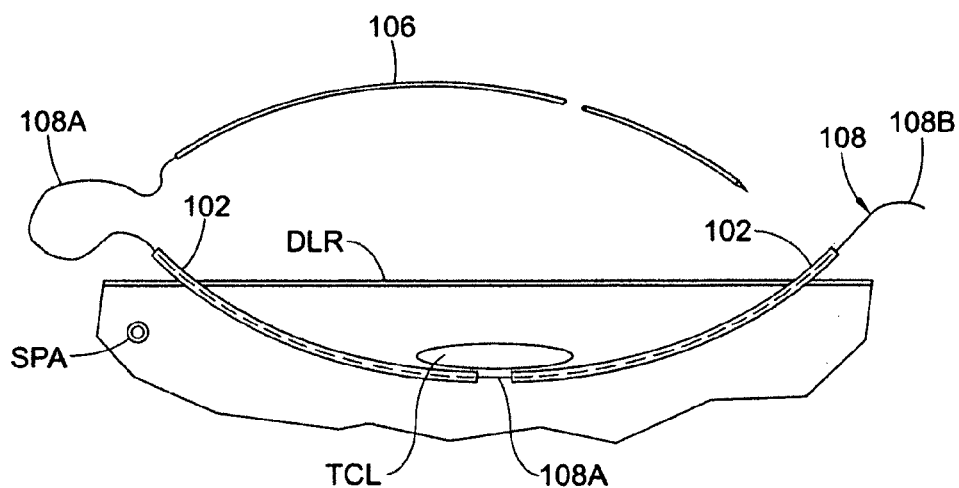

FIG. 19 illustrates solid needle 106 being passed through and out of hollow needle 102 of the second surgical device. In this manner, a first portion 108A of surgical filament 108 is drawn into and through proximal hollow needle 102, into and through distal hollow needle 102 and out of distal hollow needle 102. A second portion 108B of surgical filament 108 remains outside of the proximal hollow needle. As one example, such actions can broadly correspond to reference numbers 304 and 306 of method 300 in FIG. 15.

Figure 20:
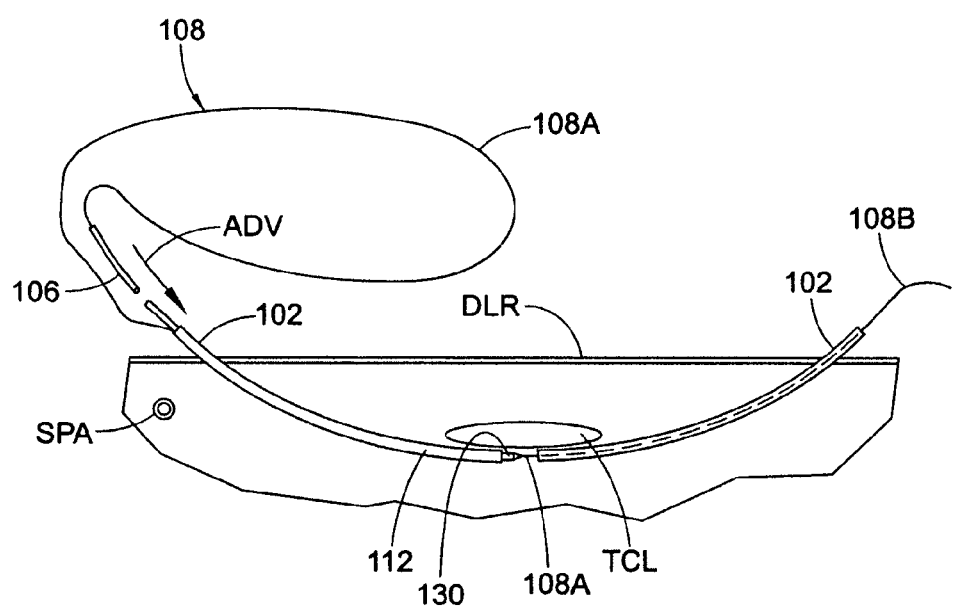

FIG. 20 illustrates solid needle 106 being advanced into distal hollow needle 102, as indicated by arrow ADV, until end 130 of the solid needle projects outwardly from end 112 of distal hollow needle 102. It will be recognized and appreciated that both solid needle 106 and a section of first portion 108A of the surgical filament are disposed within the needle passage of distal hollow needle 102, such as is illustrated in FIG. 3A, for example.

Figure 21:
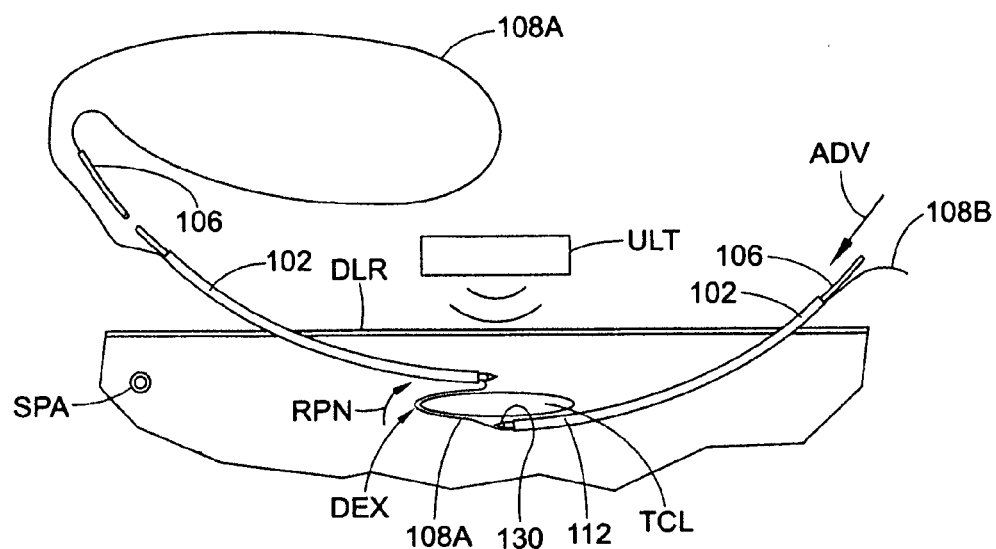

FIG. 21 illustrates solid needle 106 being advanced into proximal hollow needle 102, as indicated by arrow ADV, until end 130 of the solid needle projects outwardly from end 112 of proximal hollow needle 102. Additionally, it will be recognized an appreciated that both solid needle 106 and a section of first portion 108A of the surgical filament are disposed within the needle passage of proximal hollow needle 102, such as is illustrated in FIG. 3A, for example. FIG. 21 also illustrates the ends of distal hollow needle 102 and solid needle 106, which is received in the distal hollow needle, being repositioned from along a dorsal side of ligament TCL around distal extent DEX to an opposing palmar side of the transverse carpal ligament, as is indicated by arrow RPN. A visualization system, such as ultrasonic system ULT, can be used to guide the placement of the solid and hollow needles relative to the ligament and other tissue structures during repositioning. As one example, such repositioning actions can broadly correspond to reference number 308 of method 300 in FIG. 15.

Figure 22:
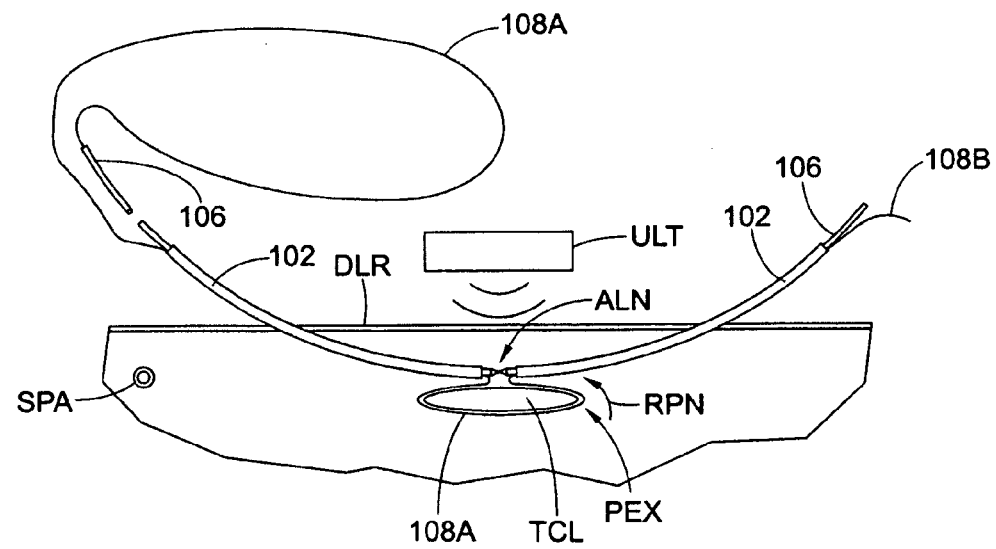

FIG. 22 illustrates the ends of proximal hollow needle 102 and solid needle 106, which is received in the proximal hollow needle, being repositioned from along a dorsal side of ligament TCL around proximal extent PEX to an opposing palmar side of the transverse carpal ligament, as is indicated by arrow RPN. A visualization system, such as ultrasonic system ULT, can be used to guide the placement of the solid and hollow needles relative to the ligament and other tissue structures during repositioning. Additionally, the visualization system can be used to at least approximately align the needle passages of hollow needles 102 with respect to one another, such as is identified in FIG. 22 by arrow ALN.

Figure 23:
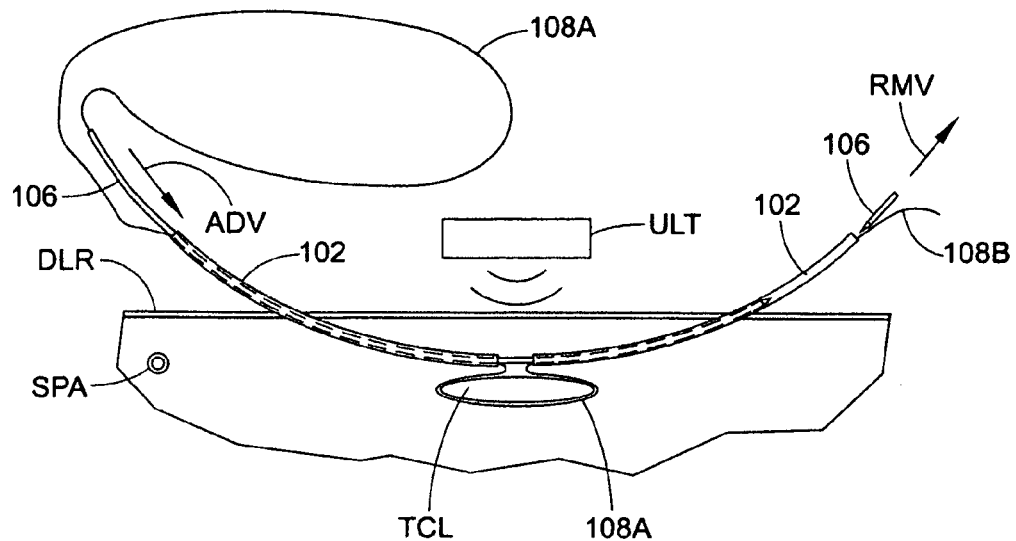

FIG. 23 illustrates solid needle 106 of within proximal hollow needle 102 being removed from the needle passage thereof, as is indicated by arrow RMV, with the proximal hollow needle remaining in position within the body tissue. Additionally, solid needle 106 within distal hollow needle 102 is shown as being advanced proximally into and along the needle passage of proximal hollow needle 102, as is indicated by arrow ADV in FIG. 23. A visualization system, such as ultrasonic system ULT, can be used to guide the entry of solid needle 106 into proximal hollow needle 102.

Figure 24:
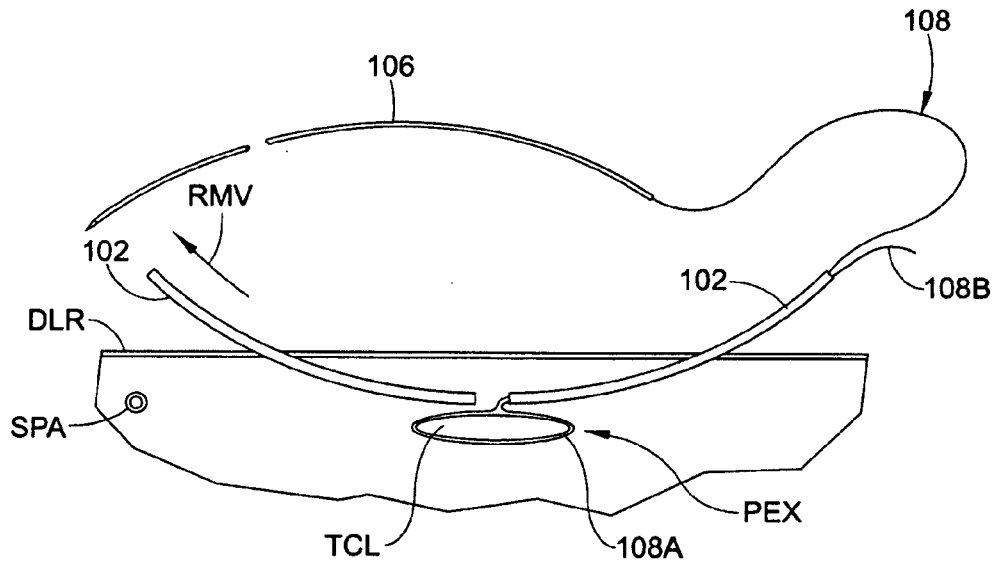

FIG. 24 illustrates solid needle 106 being passed through and out of proximal hollow needle 102. In this manner, both ends of surgical filament 108 are disposed outwardly of the body tissue and the remaining first portion 108A of surgical filament 108 can be drawn close to and form a lasso extending at least partially around the targeted tissue structure. In some cases, proximal hollow needle 102 can be repositioned such that the tip thereof is disposed adjacent proximal extend PEX of ligament TCL, such as is illustrated in FIG. 12, for example. As one example, such actions can broadly correspond to reference number 310 of method 300 in FIG. 15. Additionally, distal hollow needle 102 is removed or otherwise withdrawn from the body tissue, as is indicated by arrow RMV.

Figure 25:
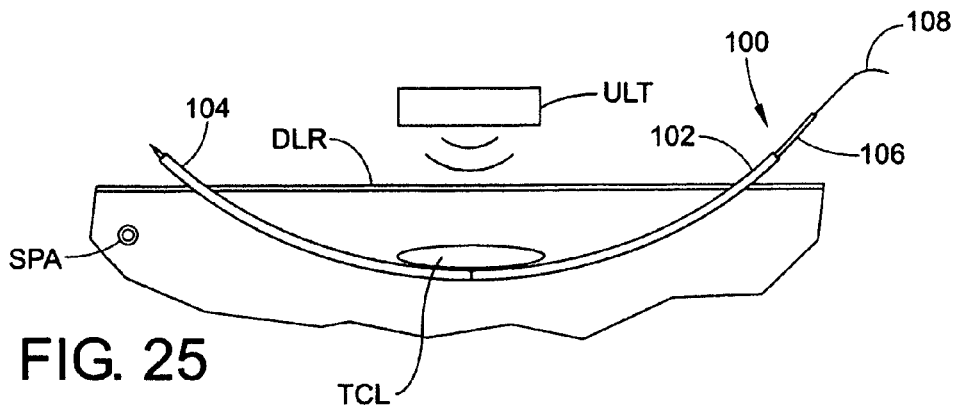
FIGS. 25-29 are cross-sectional side views, in simplified form, of the transverse carpal ligament and surrounding tissues in FIGS. 12-14 illustrating another example of a method of forming a lasso at least partially around a targeted tissue structure in accordance with the subject matter of the present disclosure.

Another example of a series of actions that can be performed to form a lasso extending at least partially around a targeted tissue structure, such as is broadly described in method 300 of FIG. 15, is illustrated in FIGS. 25-29. FIG. 25 illustrates a surgical device in accordance with the subject matter of the present disclosure, such as surgical device 100, for example, that includes a solid needle, such as solid needle 106, for example, and a plurality of hollow needles, such as hollow needles 102 and 104, for example, that are inserted together through dermal layers DRL from a point proximal to transverse carpal ligament TCL (e.g., site ST1 in FIG. 10) along the dorsal side of the ligament to an exit point distal to ligament TCL (e.g., site ST2 in FIG. 10). A visualization system, such as ultrasonic system ULT, can be used to guide the placement of the solid and hollow needles relative to the ligament and other tissue structures. As one example, such an action can broadly correspond to reference number 302 of method 300.

Figure 26:
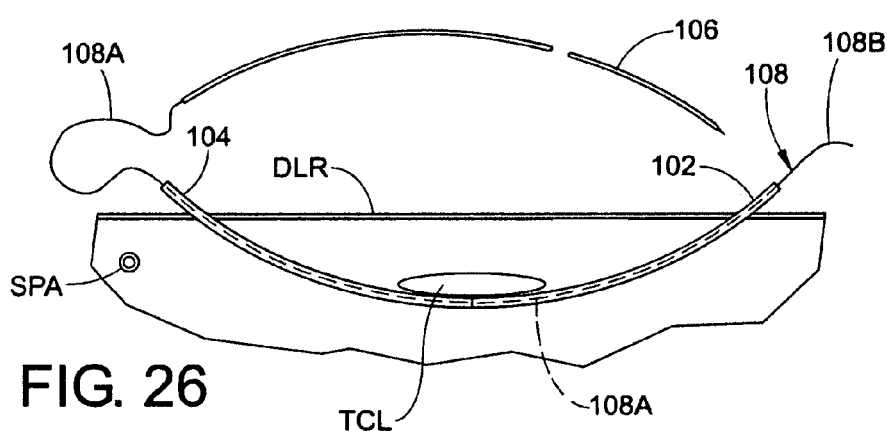

FIG. 26 illustrates solid needle 106 being passed through and out of hollow needles 102 and 104 of the surgical device. In this manner, a first portion 108A of surgical filament 108 is drawn into, through and out of hollow needles 102 and 104. A second portion 108B of surgical filament 108 remains outside of the hollow needles. As one example, such actions can broadly correspond to reference numbers 304 and 306 of method 300 in FIG. 15.

Figure 27:
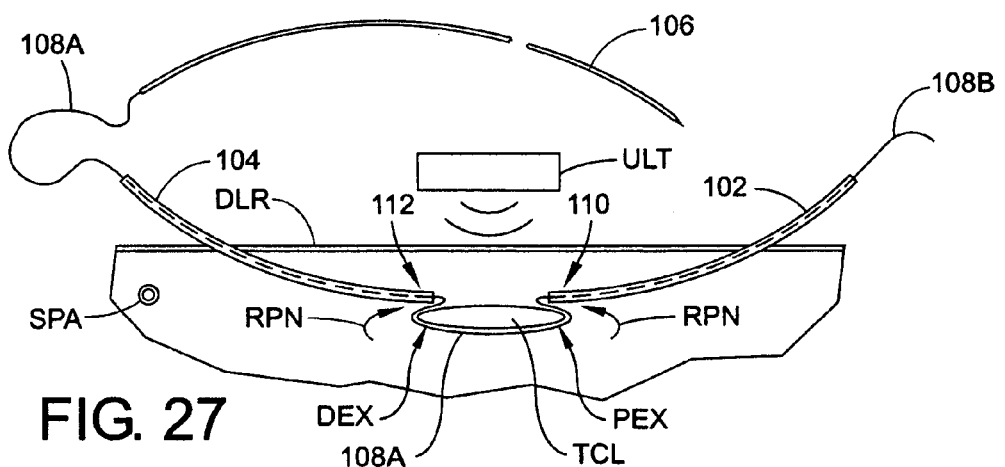

FIG. 27 illustrates the ends 110 and 112 of hollow needles 102 and 104, respectively, being repositioned from along a dorsal side of ligament TCL around proximal and distal extents PEX and DEX, respectively, to an opposing palmar side of the transverse carpal ligament, as is indicated by arrows RPN. A visualization system, such as ultrasonic system ULT, can be used to guide the placement of the hollow needles relative to the ligament and other tissue structures during repositioning. Additionally, the visualization system can be used to at least approximately align the needle passages of hollow needles 102 and 104 with respect to one another such that solid needle 106 can be advanced therethrough. As one example, such repositioning actions can broadly correspond to reference number 308 of method 300 in FIG. 15.

Figure 28:
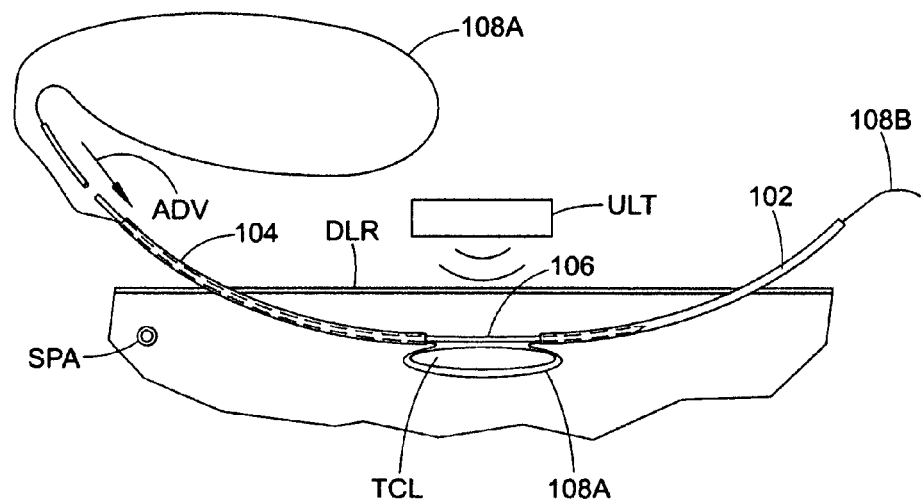

FIG. 28 illustrates solid needle 106 being advanced proximally into, along and through the needle passages of hollow needles 102 and 104, as is indicated by arrow ADV in FIG. 28. A visualization system, such as ultrasonic system ULT, can be used to guide the entry of solid needle 106 from the needle passage of hollow needle 104 into the needle passage of hollow needle 102.

Figure 29:
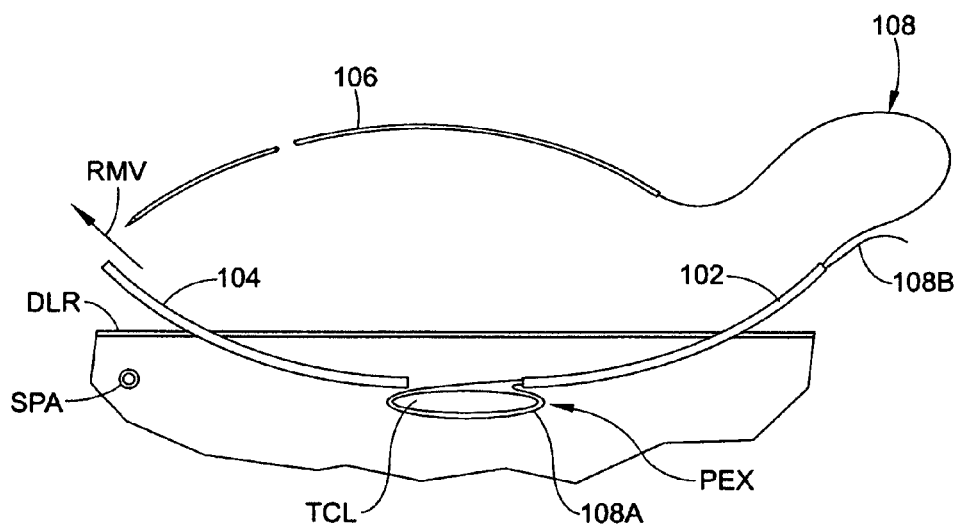

FIG. 29 illustrates solid needle 106 being passed through and out of hollow needles 102 and 104. In this manner, both ends of surgical filament 108 are disposed outwardly of the body tissue and the remaining first portion 108A of surgical filament 108 can be drawn close to and form a lasso extending at least partially around the targeted tissue structure. In some cases, hollow needle 102 can be repositioned such that the tip thereof is disposed adjacent proximal extend PEX of ligament TCL, such as is illustrated in FIG. 12, for example. As one example, such actions can broadly correspond to reference number 310 of method 300 in FIG. 15. Additionally, hollow needle 104 is removed or otherwise withdrawn from the body tissue, as is indicated by arrow RMV.

Figure 30:
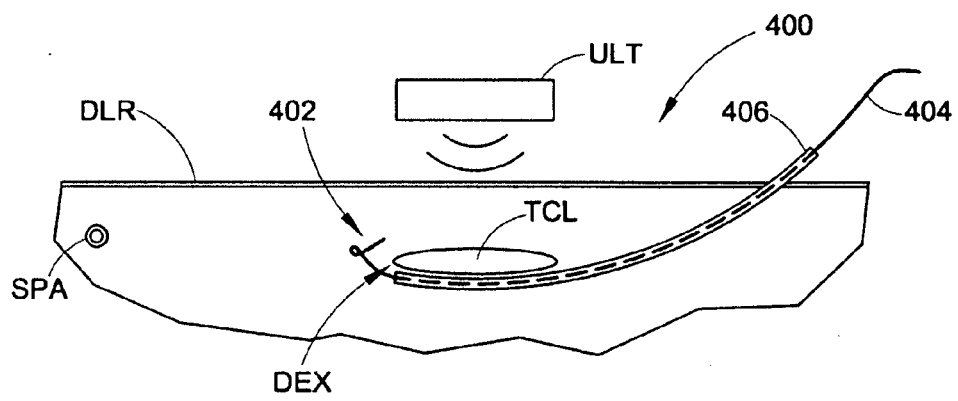
FIGS. 30-33 are cross-sectional side views, in simplified form, of the transverse carpal ligament and surrounding tissues in FIGS. 12-14 illustrating a further example of a method of forming a lasso at least partially around a targeted tissue structure in accordance with the subject matter of the present disclosure.

A further example of a series of actions that can be performed to form a lasso at least partially around a targeted tissue structure, such as is broadly described in method 300 of FIG. 15, is illustrated in FIGS. 30-33. FIG. 30 illustrates a portion of a surgical device 400 that includes a spring hook needle 402, which is attached to a surgical filament 404, and a hollow needle 406 that are inserted together through dermal layers DLR from a point proximal to transverse carpal ligament TCL (e.g., site ST1 in FIG. 10) and into the biological or body tissue along a dorsal side of ligament TCL. A visualization system, such as ultrasonic system ULT, can be used to guide the placement of the solid and hollow needles relative to the ligament and other tissue structures. Spring hook needle 402 and surgical filament 404 can be advanced to a position adjacent distal extend DEX of ligament TCL. As one example, such actions can broadly correspond to reference number 302 of method 300.

Figure 31:
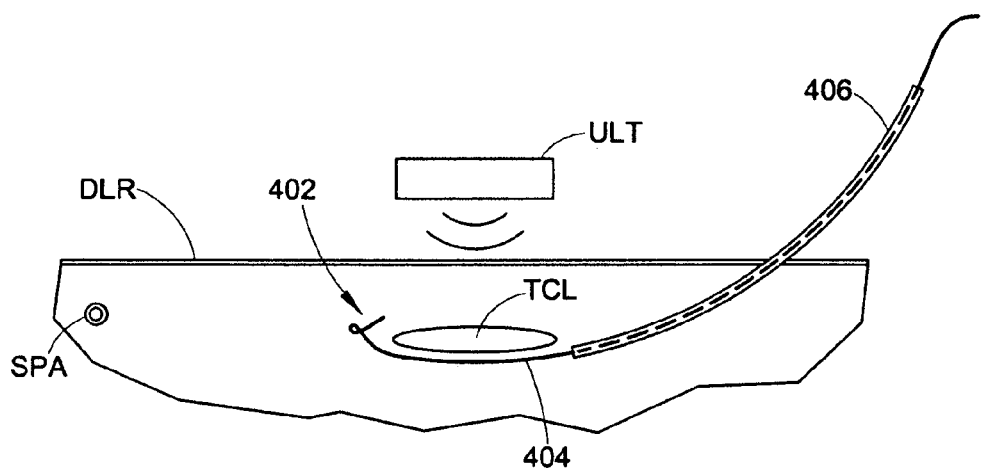

FIG. 31 illustrates hollow needle 406 being withdrawn in a proximal direction along the dorsal side of the ligament. Spring hook needle 402 and surgical filament 404 remain positioned along distal extend DEX and the dorsal side of ligament TCL. As one example, such actions can broadly correspond to reference numbers 304 and 306 of method 300 in FIG. 15. ULT can be used to confirm 402 stayed in position.

In one exemplary procedure, the hollow needle can be fully withdrawn from the body tissue, and unthreaded from the surgical filament. Alternately, as shown in FIG. 31, once in position adjacent proximal extend PEX, the end of hollow needle 406 can be repositioned from along a dorsal side of ligament TCL around proximal extent PEX to an opposing palmar side of the transverse carpal ligament, as is indicated by arrow RPN in FIG. 32. A visualization system, such as ultrasonic system ULT, can be used to guide the placement of the hollow needle 406 relative to the ligament and other tissue structures during repositioning.

Figure 32:
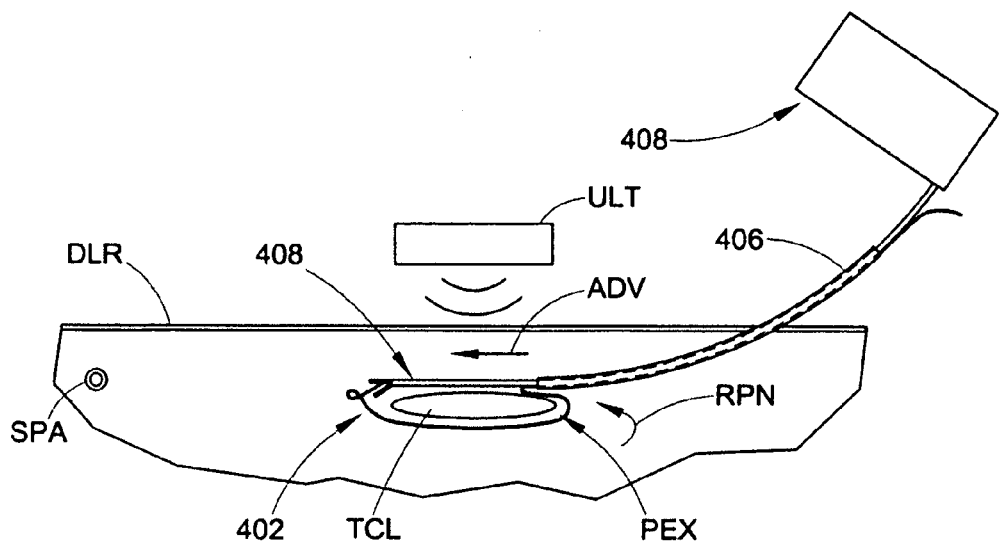

A gripper 408, such as a laparoscopic needle driver, for example, can be advanced along the palmar side of the ligament and used to grasp the spring hook for retrieval. In some cases, the gripper can be advanced directly to the ligament without the use of a hollow needle. In other cases, as shown in FIG. 32, for example, gripper 408 can be the advanced through the needle passage of hollow needle 406 together with the portion of surgical filament 404 residing therein, such as is shown in FIG. 3A, for example. In either case, the gripper can be further advanced, as is indicated by arrow ADV, toward spring hook needle 402. Gripper 408 can be selectively operated by a surgeon to grasp or otherwise secure the spring hook needle, such as is shown in FIG. 32.

Figure 33:
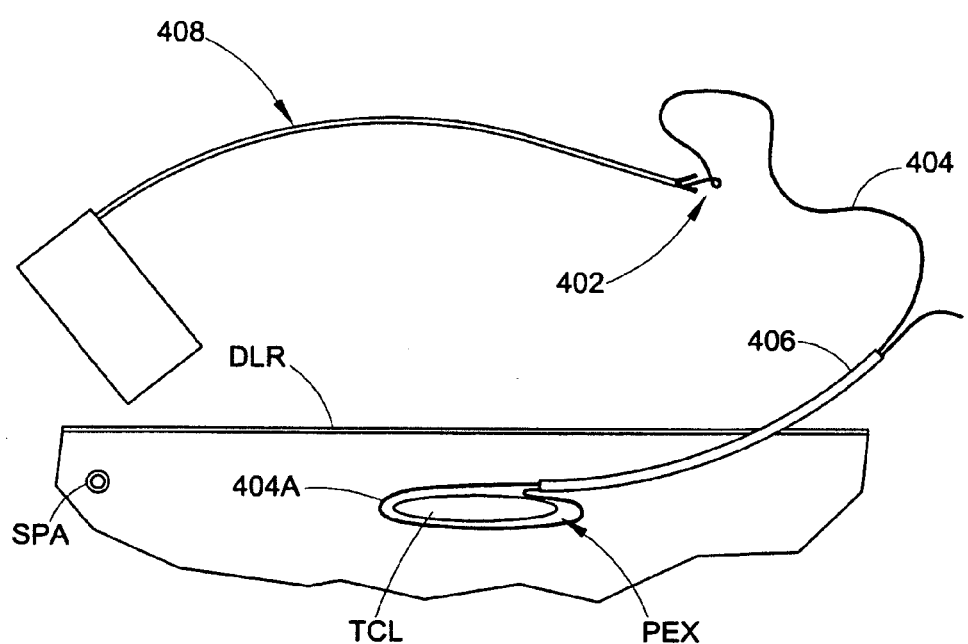

FIG. 33 illustrates gripper 408 being withdrawn from within the body tissue and pulling spring hook needle 402 from the body tissue as well. In this manner, both ends of surgical filament 404 are disposed outwardly of the body tissue and the remaining first portion 404A of surgical filament 404 can be drawn close to and substantially form a lasso extending at least partially around the targeted tissue structure. If hollow needle 406 is used, as is shown in FIG. 33, the hollow needle can be repositioned such that the tip thereof is disposed adjacent proximal extend PEX of ligament TCL, such as is illustrated in FIG. 12, for example. As one example, such actions can broadly correspond to reference numbers 308 and 310 of method 300 in FIG. 15.

As used herein with reference to certain features, elements, components and/or structures, numerical ordinals (e.g., first, second, third, fourth, etc.) may be used to denote different singles of a plurality or otherwise identify certain features, elements, components and/or structures, and do not imply any order or sequence unless specifically defined by the claim language. Additionally, the terms "transverse," and the like, are to be broadly interpreted. As such, the terms "transverse," and the like, can include a wide range of relative angular orientations that include, but are not limited to, an approximately perpendicular angular orientation.

It will be recognized that numerous different features, components, steps, actions and/or procedures are presented in the embodiments shown and described herein, and that no one embodiment may be specifically shown and described as including all such features, components, steps, actions and/or procedures. However, it is to be understood that the subject matter of the present disclosure is intended to encompass any and all combinations of the different features, components, steps, actions and/or procedures that are shown and described herein, and, without limitation, that any suitable arrangement of features, components, steps actions and/or procedures, in any combination, can be used. Thus it is to be distinctly understood claims directed to any such combination of features, components, steps, actions and/or procedures, whether or not specifically embodied herein, are intended to find support in the present disclosure.

While the subject matter of the present disclosure has been described with reference to the foregoing embodiments and considerable emphasis has been placed herein on the structures and structural interrelationships between the component parts of the embodiments disclosed, it will be appreciated that other embodiments can be made and that many changes can be made in the embodiments illustrated and described without departing from the principles of the subject matter of the present disclosure. Obviously, modifications and alterations will occur to others upon reading and understanding the preceding detailed description. Accordingly, it is to be distinctly understood that the foregoing descriptive matter is to be interpreted merely as illustrative and not as a limitation. As such, it is intended that the subject matter of the present disclosure be construed as including all such modifications and alterations insofar as they come within the scope of the appended claims and any equivalents thereof.

The invention claimed is:

1. A method of severing a targeted tissue structure embedded within biological tissue of a patient, said method comprising:
    identifying a targeted tissue structure to be severed;
    extending a passage into the biological tissue adjacent the targeted tissue structure so that said passage extends subdermally above and subdermally below the targeted tissue structure;
    forming a lasso around the targeted tissue structure using a surgical filament with at least a portion of said surgical filament extending through said passage;
    severing the targeted tissue structure using said surgical filament; and,
    retracting said surgical filament from the biological tissue through said passage.

2. A method according to claim 1 further comprising verifying the position of said surgical filament around the targeted tissue structure prior to severing the targeted tissue structure.

3. A method according to claim 1 further comprising verifying that the targeted tissue structure has been severed by said surgical filament.

4. A method according to claim 1, wherein forming a lasso around the targeted tissue structure includes inserting a hollow needle into the biological tissue adjacent the targeted tissue structure.

5. A method according to claim 4, wherein forming a lasso around the targeted tissue structure includes drawing a first portion of said surgical filament into the biological tissue through said hollow needle while a second portion of said surgical filament remains outside the biological tissue.

6. A method according to claim 5, wherein forming a lasso around the targeted tissue structure includes positioning said first portion of said surgical filament along one side of the targeted tissue structure, and extending said first portion of said surgical filament around the targeted tissue structure and along an opposing side of side of the targeted tissue structure.

7. A method according to claim 6, wherein forming a lasso around the targeted tissue structure includes drawing at least part of said first portion of said filament structure out of the biological tissue through said hollow needle.

\* \* \* \* \*